United States Patent [19]

Masuda et al.

[11] Patent Number: 5,300,421

[45] Date of Patent: Apr. 5, 1994

[54] METHOD FOR QUANTITATIVE MEASUREMENT OF TRACE ENZYME AND SUBSTRATE USED THEREIN

[75] Inventors: Nobuhito Masuda; Nobuo Suzuki; Shoji Ishiguro; Mitsunori Ono, all of Asaka, Japan

[73] Assignee: Fuji Photo Film Co., Ltd., Kanagawa, Japan

[21] Appl. No.: 727,347

[22] Filed: Jul. 8, 1991

Related U.S. Application Data

[63] Continuation of Ser. No. 368,615, Jun. 20, 1989, abandoned.

[30] Foreign Application Priority Data

Jun. 20, 1988 [JP] Japan ................... 63-151802

[51] Int. Cl.$^5$ ................ C12Q 1/00; G01N 33/53
[52] U.S. Cl. ...................... 435/4; 435/7.4; 435/7.5; 435/14; 435/23; 436/170; 422/56
[58] Field of Search ............ 435/4, 7.4, 7.5, 14, 435/23, 38, 94, 186, 193; 8/549; 264/4.3; 436/170; 422/56; 530/331

[56] References Cited

U.S. PATENT DOCUMENTS 4,414,323  11/1983  Masuda et al. ............ 435/7.4
4,414,325  11/1983  Masuda et al. ............ 435/7.4
4,966,607  10/1990  Shinoki et al. ............ 8/549

OTHER PUBLICATIONS

*Pharmacia Fine Chemicals* (1983) Affinity Chromatography, p. 4.

Primary Examiner—Michael G. Wityshyn
Assistant Examiner—Abdel A. Mohamed
Attorney, Agent, or Firm—Sughrue, Mion, Zinn, Macpeak & Seas

[57] ABSTRACT

A synthetic substrate used for quantitative analysis of a trace enzyme. The substrate has a molecular structure (B)-(A)-(C) comprising at least one structure (A) catalytically affected by the enzyme to be analysed, at least one photographically active labelling structure (B) linked to the structure (A) and at least one specific adsorbing structure (C) linked to the structure (A). The substrate is used in a quantitative analysis of a trace enzyme, in which the structure (A) or the linkage between the structure (A) and the structure (C), or the linkage between the structure (B) and the structure (A) is cleaved by the action of the analyte enzyme. The reaction product of the enzymatic reaction is separated by allowing the same to contact with an adsorbent for the structure (C). The separated reaction product is developed photographically and then the optical density of the resultant developed silver and/or colored dye is measured.

21 Claims, No Drawings

METHOD FOR QUANTITATIVE MEASUREMENT OF TRACE ENZYME AND SUBSTRATE USED THEREIN

This is a continuation of application Ser. No. 07/368,615, filed Jun. 20, 1989, now abandoned.

BACKGROUND OF THE INVENTION

1. Field of the Invention

The present invention relates to a method for quantitative measurement of a trace enzyme, and particularly to a method for photochemical measurement of the activity of a trace enzyme and a substrate used therein.

2. Prior Art Statement

Various methods have hitherto been developed for measuring the activity of a trace enzyme. For example, there are: a turbidimetric method wherein the decrease in turbidity caused by an enzyme reaction is traced using a suspension of high molecular weight substrate; an absorptiometric method wherein a high molecular weight substrate is decomposed or cleaved by an enzyme and, after precipitating and removing undecomposed substrate, soluble component is determined by an absorbance measurement; a method wherein a dye or fluorescent substance is previously bound to a high molecular weight substrate, an enzymatic reaction is effected to decrease the molecular weight of the dye or fluorescent substance, and the fractionated dye or fluorescent substance of lower molecular weight is measured; and a method of quantitative assay wherein, using a substrate which is designed to change in absorption spectrum, one forms a color or forms a fluorescent substance, based on a splitting-off or change in part of the substrate after an enzymatic reaction, and the resulting absorbancy or fluorescent intensity is measured, etc. (SEIKAGAKU JIKKEN KOZA (Lectures on Biochemical Experiments), vol. 5, subtitled "Study on Enzymes", edited by the Japanese Biochemical Society, published by Tokyo Kagaku Dojin, 1975.)

Most of these methods, however, quantitatively determine an amount of enzyme on the order of, $\mu g/ml$. Even utilizing a type of substrate releasing a fluorescent substance (e.g. derivatives of umbelliferone, etc.), which is recognized to be most sensitive among these conventional methods, it is only possible to measure an enzyme quantity on the order of ng/ml.

Therefore, in activity measurements of trace enzymes labelled in accordance with an enzyme immunoassay, the development of more stable and more highly sensitive enzyme activity measurement methods has been demanded.

Further, since the enzymes as biocomponents in blood, body fluids, urine and in tissues in the living body such as various organs, the brain, etc. mostly are present in a very small amount, except for certain enzymes (amylase, GOT, GTP, etc.) which exist in a large amount, such enzymes cannot be determined by conventional measurement methods. Therefore, a radioimmunoassay (hereinafter referred to as "RIA") which is an immunological measurement method using a radioactive isotope has recently been introduced. The principle of RIA is described in, for example, Kumahara and Shizume, RADIOIMMUNOASSAY, New Edition, pages 3 to 10 (1977), published by Asakura Publishing Co., Ltd., KISO SEIKAGAKU JIKKENHO (Basic Biochemical Experiments) (6), Biochemical Assay (1967), published by Maruzen Co., Ltd., Tokyo, METHODS IN ENZYMOLOGY, edited by Sidney P. Colowick et al., vols. I, II, III, V and VII, published by Academic Press, New York and The Enzyme, vols. 3, 4 and 5, Paul D. Boyer et al. (1071), published by Academic Press, New York.

However, RIA as a quantitative assay for enzymes has disadvantages such as: (1) since it is an immunoassay which detects a quantity of enzyme, there is a possibility that the activity of an enzyme -which is the functional characteristic of the enzyme- will not be actually reflected; (2) there is a possibility that analogous enzymes and precursors having a similar antigenic site might be included in analytical data; and (3) in the case where the enzyme to be measured, for example, such a label enzyme used for the enzyme immunoassay, is bound to another component and not present in the free state, it is difficult to prepare an antibody against the aforesaid labelled antigen or antibody and the design for a method for measurement is practically difficult.

RIA has further disadvantages due to the use of radioisotopes. That is: (1) potential injury to the person dealing with radiation is a matter of concern; (2) special places and controls are required for storage and waste disposal of the radioactive substances used; (3) the amount of radiation from the radioisotope is reduced with the passage of time due to the half decay of the isotope; and (4) measurement of the amount of radioactivity requires expensive devices.

The information obtained by measuring enzyme activity using a specific substrate under given reaction conditions (e.g. concentration of substrate, total volume, reaction pH, reaction temperature, reaction time, ionic strength, salts co-existent, etc.) is generally classified as follows.

(1) The sum of enzyme activities having a catalytic action on the structure of the substrate in the system; or (2) Under the condition of constant enzyme concentration, the degree of inactivation depending upon purity of the enzyme, the presence or absence of inhibitors, intensity of inhibition, denaturation, etc., i.e. measure of specific activity.

Finally, the purpose of measuring the activity of an enzyme as a component in the living body is frequently to obtain mainly information per (1) above and the purpose of activity measurements of enzyme-labelled materials exterior living body is to obtain mainly information per (1) and (2) above. As is well known, in any case, specific enzyme to the living body is to obtain mainly information per (1) and (2) above. As is well known, in any case, specific enzyme activity can only be measured by selecting a substrate corresponding to the enzyme specificity.

The term "specificity" used throughout the specification is art-recognized and defines selective reactivity between substances, e.g. of an enzyme with its corresponding substrate.

Japanese Patent Publication Nos. 1118/1986 (U.S. Pat. No. 4,414,325) and 1119/1986 (U.S. Pat. No. 4,414,323) disclose a method for quantitative measurement of a trace enzyme, wherein an enzyme substrate having therein a photographically active material (a spectroscopically sensitizing dye or a fogging agent) as a labelling material is used so that the activity of a trace enzyme is photochemically determined.

The method disclosed in U.S. Pat. No. 4,414,323 is a method for measurement of an emzyme activity and/or a quantity of an enzyme comprising the steps of providing a synthetic substrate comprising at least one photographically active labelling structure (B) serving as a labelling material by contacting it with silver halide grains to form nuclei capable of being developed (a spectroscopically sensitizing dye or a nucleating agent (fogging agent)) and at least one structure (A) to be specifically contacted with the enzyme to be measured; bringing either the reaction product containing the photographically active labelling structure (B) formed by the enzyme reaction or the unreacted synthetic substrate into contact with silver halide followed by development; and measuring the amount of developed silver and/or the amount of colored dye obtained as an optical density.

The method referred to in the preceding paragraph provides not only a very high sensitivity but also is effectively applied to the situation where an enzyme is in the form of a conjugate or complex thereof with other organic materials (e.g. polymers, latexes, microcapsules, membranes including membranes in living bodies and ion exchange membranes, bacteria, microorganisms, components in living bodies such as hormones, peptides, proteins, lipoproteins, glycoproteins, glucosides and lipids, toxic substances, drugs, antibiotics, etc.).

In a method for quantitative determination of an enzyme activity, the sensitivity of the method depends mainly on the following two factors. The first factor is the absolute sensitivity of the substance used for generating the detected signal, and the second factor is how to detect the signal from the product of the enzymatic reaction.

As to the absolute sensitivity limited by the used substance, the limit for detection is an the order of $10^{-6}$ mole/l when a dye is used as the product of the enzymatic reaction, and the limit for detection is an the order of $10^{-9}$ mole/l when a fluorescent material is used as detectable signal. On the other hand, when a photographically active material is used as above-described, the limit for detection is improved to the order of $10^{-11}$ mole/l.

In the actual determination of an enzyme activity while using a photographically active material, the limit for detection depends on the density of the produced signal material which is detectable as having a significant difference from the background. In the colorimetric method wherein a dye is used, the density of the background does not affect the result of determination and the sensitivity of the method is affected only by the molecular absorption coefficient of the used signal material. In the method wherein a fluorescent material is used, the density of the background is often increased by the purity of energized light, dusts contained in the medium, entangled particles, dispersed materials or contamination of other fluorescent materials to lower the sensitivity to the order of $10^{-8}$ mole/l. The sensitivity of the method wherein a photographically active material is used depends on the purity of the product of the enzymatic reaction separated from the unreacted synthetic substrate.

In the method wherein a photographically active material is used, contamination with materials exhibiting similar functions as that of the used photographically active material need not be taken into account in view of the structure of the photographically active material. This is because the background is induced by the contaminating unreacted synthetic substrate in the step of detecting the photographically active material in the product of the enzymatic reaction. In general, a substrate is used in a concentration of from $10^{-2}$ to $10^{-6}$ mole/l in ordinary enzymatic reaction, and the substrate is used in a relatively high concentration when a trace enzyme is to be detected. Although $10^{-7}$ to $10^{-9}$ mole/l of a product of the enzymatic reaction should be detected in the low sensitivity range ($10^{-7}$ to $10^{-9}$ mole/l), separation can be effected relatively easily by the conventional methods wherein the differences in chemical and physical properties between the reaction product of the enzymatic reaction and the unreacted synthetic substrate are detected. For example, both components may be separated from each other, utilizing their difference in absorptive property to silver halide or using another proper separation method (for example, ion exchange chromatography, affinity chromatography, high speed liquid chromatography, TLC, salting out, centrifugal separation, co-precipitation with a polymer, decantation, ultrafiltration, use of an adsorbent such as activated charcoal, etc.) The details thereof are described in DATABOOK OF BIOCHEMISTRY, Chapter 10, second separate volume, edited by Japanese Biochemical Society, published by tokyo Kagaku Dojin, 1980.

In the maximum sensitivity range, it is necessary to detect $10^{-9}$ to $10^{-11}$ mole/l of a reaction product of enzymatic reaction. Namely, it becomes necessary to separate $10^{-9}$ to $10^{-11}$ mole/l of a pure reaction product from a solution or suspension containing $10^{-2}$ to $10^{-6}$ mole/l of a synthetic substrate.

SUMMARY OF THE INVENTION

The present invention provides a synthetic substrate to enable separation of a trace amount of a reaction product of an enzymatic reaction quantitatively in a pure state from a large excess of the unreacted substrate so as to realize ultra-high sensitivity of a method using a photographically active material.

After eager pursuit for developing a method for separating an enzymatic product on the order of $10^{-8}$ to $10^{-11}$ mole/l from a synthetic substrate on the order of $10^{-2}$ to $10^{-6}$ mole/l so as to take advantage of high sensitivity of the method wherein a photographically active material is used, we have found that such separation can be achieved by the utilization of a specific absorption reaction having a sufficiently high association constant.

The substrate for use in a quantitative measurement, provided by the present invention, is characterized by the molecular structure which comprises at least one structure (A) specifically catalytically affected by the enzyme to be assayed, at least one photographically active labelling structure (B) linked to said structure (A) and at least one specific adsorbing structure (C) linked to said structure (A).

According to a further aspect of the invention, there is provided a method for assaying a sample for quantitative determination of an enzyme activity and/or a quantity of an enzyme comprising the steps of:

(a) providing a substrate having a molecular structure which comprises at least one structure (A) catalytically affected by the enzyme to be assayed, at least one photographically active labelling structure (B) linked to said structure (A) and at least one specifically adsorbing structure (C) linked to said structure (A);

(b) contacting a sample with said substrate so as to bring about a chemical reaction by said enzyme;

(c) separating the reaction product containing said photographically active labelling structure (B) from the excess unreacted substrate by the utilization of the specific adsorbing property of the structure (C);

(d) contacting either the reaction product separated at the step (c) or the excess unreacted substrate separated at the step (c) with silver halide;

(e) photographycally developing either product resulting from the step (d); and (f) measuring the optical density of the silver image and/or the colored dye resulting from the step (e).

Upon contact with an enzyme to be measured, the aforesaid synthetic substrate, which has at least one for each of the structures (A), (B) and (C), and in which the structure (B) is linked through the structure (A) with the structure (C), is attacked by the enzyme and is cleaved, whereby a derivative of the structure (B) deprived of the structure (C) is formed. Then, a sufficiently excess amount of an adsorbent having a specific adsorption property for the structure (C) is added to leave the derivative of the structure (B) deprived of the structure (C) in the unadsorbed or free state. After the derivative of the structure (B) deprived of the structure (C) is allowed to be contacted with silver halide and then developed, the quantity of developed silver and/or the quantity of colored dye is determined by measuring the optical density which is compared with a separately drawn calibration curve to find the quantity or concentration of the enzyme to be measured. Alternatively, the decrease in quantity of substrate, which corresponds to the quantity of the enzyme to be measured, may be determined by desorbing the unreacted synthetic substrate adsorbed to the adsorbent by proper means.

The principle of the method of this invention may be summarized by the following scheme:

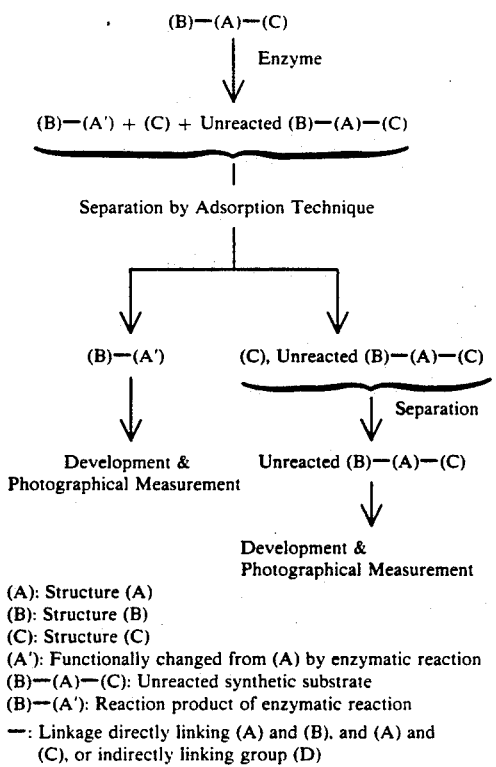

(A): Structure (A)
(B): Structure (B)
(C): Structure (C)
(A'): Functionally changed from (A) by enzymatic reaction
(B)—(A)—(C): Unreacted synthetic substrate
(B)—(A'): Reaction product of enzymatic reaction
—: Linkage directly linking (A) and (B), and (A) and (C), or indirectly linking group (D)

DESCRIPTION OF THE PREFERRED EMBODIMENTS

Enzyme to Be Measured by the Invention

Enzymes which are to be measured in accordance with this invention are known, depending upon mode of contact in enzymatic reaction, as hydrolase type enzymes (e.g. protease, nuclease, glycogenase, esterase, lipase, etc.), which cleaves bonds in substrate molecules, a peptide bond, ester bond, phosphate bond, glucoside bond, acid amide bond, etc., by the addition of a water molecule; so-called eliminase and transferase type enzymes which release a specific functional group contained in substrates or transfer it to another substrate; electron transfer type enzymes which contribute to the transfer of oxygen to the substrates; redox type enzymes which contribute to the redox reaction of the substrates, etc.

Representative examples of enzymes which are objectives to be assayed in accordance with the method of this invention include proteases such as trypsin, plasmin, kallikrein, thrombin, chymotrypsin, urokinase, catepsin, strephomycin alkali protease, papain, ficin, bromelain, renin, collagenase, erastase, etc.; peptidoses such as leucine aminopeptidase, aminopeptidase, acylamino acid releasing enzyme, carboxypeptidase, dipeptidyl peptidase, etc.; nucleases such as ribonuclease A, ribonuclease $T_1$, deoxyribonuclease $A_1$, endonuclease, etc.; glycogenase including lyase type enzymes such as amylase, lysozyme, glucosidose, galactosidase, mannosidase, phosphorylase, glucanase, hyaluronidase, chondrotinase, arginic acid lyase, etc.; lipases such as lipase, phospholipase, etc.; transferases such as transcarbamylase, aminotransferase, acyltransferase, phosphotransferase, etc.; and lyases such as carboxylase, hydrolyase, ammonialyase, etc.

Such enzymes are described in detail, for example, in ENZYME, edited by Masaru Funatsu, published by Kodansha Publishing Co., Ltd., 1977, DATABOOK OF BIOCHEMISTRY, first & second separate volumes, edited by Japanese Biochemical Society., published by Tokyo Kagaku Dojin, 1979 & 1980, The Enzyme, vols. III, IV and V, Paul D. Boyner et al., 1971, published by Academic Press, New York.

Structure (A)

The structure (A) used in this invention which is specifically contacted with an enzyme to be measured, generally comprises a contact site for an enzyme and a recognition site or binding site for the enzyme. Such contact sites for the enzyme are, for example, a peptide bond (acid-amide bond), ester bond, a phosphate ester bond or a glucoside bond for hydrolase enzymes. Other examples are an amino group, a carboxy group, etc. for transferase enzymes. An amino acid residue, sugar, a nucleic acid base, etc. are examples which may be used as the recognition or binding site for the enzyme. These are more specifically described, for example, in DATABOOK OF BIOCHEMISTRY, first and second separate volumes, edited by Japanese Biochemical Society, published by Tokyo Kagaku Dojin, 1979 & 1980, and the Enzyme, vols. III, IV and V edited by Paul D., Boyer et al., published by Academic Press, 1971, as substrate structures corresponding to the substrate specificity of the enzyme.

Structure (B)

The photographically active labelling structure (B) in the substrate used in this invention includes materials capable of forming developable nuclei upon contact with silver halide grains, which are known in the field of silver halide photochemistry as nucleating agents.

Details of such materials are described in T. H. James, THE THEORY OF THE PHOTOGRAPHIC PROCESS, 4th ed., pp 393-395 (1977), published by MacMillan Co., Ltd.

More specific examples thereof will be set forth below.

1. Compounds each containing a cyclic or acyclic thiocarbonyl group (e.g. thioureas, dithiocarbonates, trithiocarbonates, dithioesters, thioamide, rhodanines, thiohydantoins, thiosemicarbazides, or derivatives thereof);

2. Compounds each containing a cyclic or acyclic thio ether group (e.g. sulfides, disulfides, polysulfides, etc.);

3 Other sulfur-containing compounds (e.g. thiosulfates, thiophosphates, and compounds derived therefrom);

4. Nitrogen-containing reducible compounds (e.g. hydrazines, hydrazones, amines, polyamines, cyclic amines, hydroxylamines, quarternary ammonium salt derivatives, etc.);

5. Reducible compounds (e.g. aldehydes, sulfinic acids, enediols, metal hydride compounds, alkyl metals, aromatic compounds in dihydro form, active methylene compounds, etc.);

6. Metal complexes (e.g. four-coordinate Ni(II) or Fe(II) complexes having sulfur as a ligand, etc.);

7. Acetylene compounds; and

8. Others (e.g. phosphonium salts, etc.)

The order of preference in these compounds is, in succession, 4, 5 and 6 as the most preferred group, and then 1, 2, 7 and 3 as the second most preferred.

(II-1) Specific examples of the compounds which are particularly preferably used as the structure (B) in this invention include compounds represented by the following general formula (N-I) of:

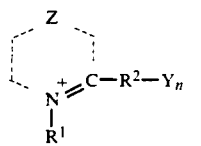

(N-I)

In the general formula (N-I) set forth above, Z is a non-metallic element necessary for forming a heterocyclic five- or six-member ring and may be substituted by a substituting group. $R^1$ is an aliphatic group, and $R^2$ is a hydrogen atom, an aliphatic or an aromatic group. Y is a counter-ion for balancing the electric charge, and n is zero or 1. Either one or both of the groups $R^1$ and $R^2$ may be substituted by a substituting group. However, at least one of $R^1$, $R^2$ and Z contains an alkynyl group, acyl group, hydrazine group or hydrazone group, or a six-member ring is formed by $R^1$ and $R^2$ to form a skeletal chain of dihydropyridinium. At least one of the substituting groups bound to $R^1$, $R^2$ and Z may be represented by $X^1$-$(L^1)_m$ wherein $X^1$ is a group promoting adsorption of structure (B) to silver halide, $L^1$ is a divalent linkage group, and m is zero or 1.

More specifically, examples of the heterocyclic groups containing the element Z are quinolinium, benzothiazolium, benzimidazolium, pyridium, thiazolium, naphthoorazolium, selenazolium, benzoselenazolium, imidazolium, tetrazolium, indolenium, pyrrolidinium, acrydinium, phenathridinium, isoquinolinium, oxazolium, naphthoorazolium and benzoxazolium. Examples of the substituting group or groups for the element Z include alkyl groups, alkenyl groups, aralkyl groups, aryl groups, alkynyl groups, hydroxy groups, alkoxy groups, aryloxy groups, halogen atoms, amino groups, alkylthio groups, arylthio groups, acyloxy groups, acylamino groups, sulfonyl groups, sulfonyloxy groups, sulfonylamino groups, carboxyl groups, acyl groups, carbamoyl groups, sulfamoyl groups, sulfo groups, cyano groups, ureido groups, urethane groups, carbonic acid ester groups, hydrazine groups and imino groups. At least one of the substituting groups set forth above is selected as a substituting group bound to the element Z, or two or more same or different groups may be bound to Z. The substituting groups may also be substituted additionally by any one or more of the substituting groups set forth above.

Furthermore, the substituting group bound to Z may have a heterocyclic quaternary ammonium group including the element Z and having an appropriate linking group L. In this case, the compound has a so-called dimer structure.

Preferable examples of the heterocyclic rings including the element Z are a quinolinium ring, benzothiazolium ring, benzimidazolium ring, pyridinium ring, acridinium ring, phenanthridinium ring and isoquinolinium ring. Among them, more preferable examples are a quinolinium ring, benzothiazolium ring and benzimidazolium ring, further more preferable examples are a quinolinium ring and benzothiazolium ring, and the most preferable example is a quinolinium ring.

Each of the aliphatic groups $R^1$ and $R^2$ is an unsubstitutred alkyl group having 1 to 18 carbon atoms, or a substituted alkyl group having an alkyl chain constituted of 1 to 18 carbon atoms. The substituting groups for the groups $R^1$ and $R^2$ include those referred to as the substituting groups for the element Z. The aromatic groups used as the group $R^2$ include aromatic groups having 6 to 20 carbon atoms, such as a phenyl group and naphtyl group. The substituting groups for the group $R^2$ include those referred to as the substituting groups for the element Z.

At least one of the groups $R^1$ and $R^2$ and the element Z contains alkynyl group, acyl group, hydrazine group or hydrazone group, or a six-member ring is formed by $R^1$ and $R^2$ to form a skeletal structure of dihydropyridinium. These groups may be substituted by any one or more substituting groups referred to as the substituting groups for Z.

It is preferred that the hydrazine group contains an acyl group or a sulfonyl group as a substituting group.

It is preferred that the hydrazane group contains an aliphatic or aromatic group as a substituting group.

Examples of preferable acyl groups are formyl group and an aliphatic or aromatic ketone.

Some of the alkynyl substituting groups contained more of $R^1$, $R^2$ and Z have been already described. In detail, preferable alkynyl groups include those having 2 to 18 carbon atoms, the specific examples being an ethynyl group, propargyl group, 2-butynyl group, 1-methylpropargyl group, 1,1-dimethylpropargyl group, 3-butynyl group and 4-pentynyl group. The most preferable compound is formed when the substituting group of $R^1$ is propargyl group.

The alkynyl substituting groups may be substituted by any of the substituting groups referred to as the substituting groups for Z. Examples of substituted alkynyl groups are a 3-phenylpropargyl group, 3-methoxycarbonylpropargyl group and 4-methoxy-2-butynyl group.

It is preferred that at least one of the substituting groups for $R^1$, $R^2$ and Z is alkynyl group or acyl group, or the group $R^1$ and $R^2$ is coupled to form a dihydropyridinium skeletal structure. The most preferred are the compounds wherein at least one alkynyl group is in the substituting group for the groups $R^1$ or $R^2$ or the ring containing Z.

The group $X^1$ for promoting adsorption of the structure (B) to silver halide includes, for example, thioamide group, mercapto group and five-member or six-member nitrogen-containing heterocyclic ring.

Thioamide groups used as the group $X^1$ is a divalent group represented by

—C-amino-, and may be a portion of the ring structure or may be non-cyclic thioamide group. Usable thioamide adsorption promotors may be selected from those disclosed in U.S. Pat. Nos. 4,030,925, 4,031,127, 4,080,207, 4,245,037, 4,255,511, 4,266,013 and 4,276,364 and "Research Disclosure", vol. 151, No. 15162 (November of 1976) and "Research Disclosure", vol. 176, No. (December of 1978).

Specific examples of acyclic thioamide groups include thioureide group, thiourethane group and dithiocarbamic acid ester group; and the specific examples of cyclic thioamide groups include 4-thiazoline-2-thione, 4-imidazoline-2-thione, 2-thiohydantoin, rhodanine, thiobarbituric acid, tetrazoline-5-thione, 1,2,4-triazoline-3-thione, 1,3,4-thiazoline-2-thione, 1,3,4-oxadiazoline-2-thione, benzimidazoline-2-thione, benzoxazoline-2-thione and benzothiazoline-2-thione. These groups may be further substituted.

The mercapto group represented by $X^1$ may be formed by introducing —SH group directly to $R^1$, $R^2$ or Z or may be formed by introducing —SH group to a substituting group bound to $R^1$, $R^2$ or Z. Eventually, examples of the mercapto group include aliphatic mercapto groups, aromatic mercapto groups and heterocyclic mercapto groups. (When a nitrogen atom is present adjacent to the carbon atom to which the —SH group is bound, the number of the mercapto groups is the same as the cyclic thioamide groups which is tautomeric thereto, the specific examples being set froth hereinbefore.)

Examples of the five-member or six-member nitrogen-containing heterocyclic ring represented by $X^1$ include five-member or six-member nitrogen-containing heterocyclic rings containing nitrogen, oxygen, sulfur and carbon in combination. Preferable examples are benzotriazole, triazole, tetrazole, indazole, benzimidazole, imidazole, benzothiazole, thiazole, benzooxazole, oxazole, thiadiazole, oxadiazole and triazine. These rings may be substituted by appropriate substituting groups. Preferable substituting groups are the same as set forth hereinbefore as the substituting groups for Z. More preferable nitrogen-containing heterocyclic rings are benzotriazole, triazole, tetrazole and indazole, the most preferable being benzotriazole.

The divalent linkage groups represented by $L^1$ are atoms or atom groups each containing at least one of C, N, S and O. Specific examples include an alkylene group, alkenylene group, alkynylene group, arylene group, —O—, —S—, —NH—, —N=, —CO— and —SO$_2$—. These groups may be substituted and may be used singly or in combination.

The counter-ion Y for balancing the electric charge is an arbitrary negative ion for cancelling the positive charge due to the presence of a quarternary ammonium salt in the heterocyclic ring, the specific examples being bromine ion, chlorine ion, iodine ion, p-toluene sulfonic acid ion, ethylsulfonic acid ion, perchloric acid ion, trifluoromethanesulfonic acid ion and thiocyan ion. In this case, n takes the value of 1. When the quarternary ammonium salt contained in the heterocyclic ring includes a negative ion substituting group, such as a sulfonalkyl substituting group, the salt may be in the form of a betaine. In such a case, the counter-ion Y is not required and n takes the value of zero. When the quarternary ammonium salt contained in the heterocyclic ring includes two negative substituting groups, for example two sulfonalkyl groups, Y is a positive counter-ion and may be an alkali metal ion (sodium ion or potassium ion, etc.) or an ammonium salt (triethylammonium, etc.).

Specific examples of the compound represented by the general formula (N-1) will be set forth below.

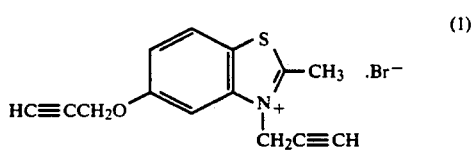
(1)

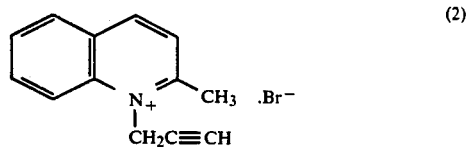
(2)

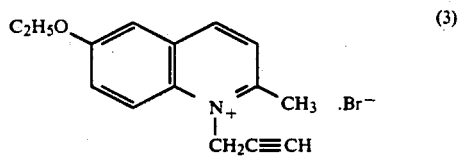
(3)

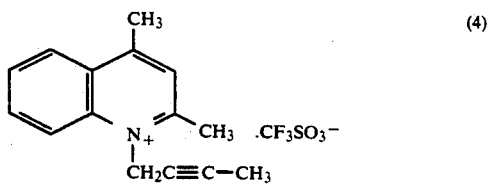
(4)

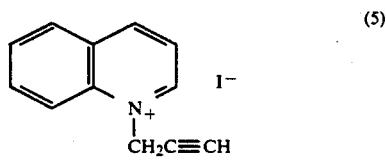
(5)

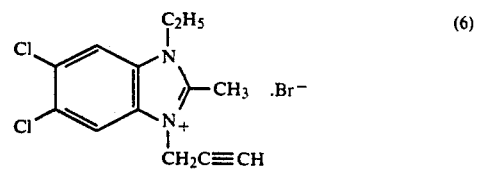
(6)

-continued
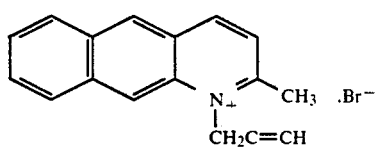 (7)
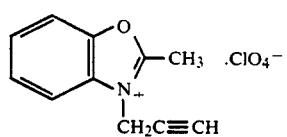 (8)
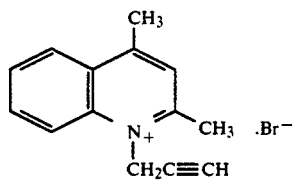 (9)
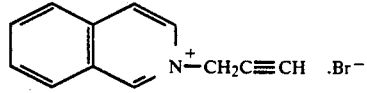 (10)
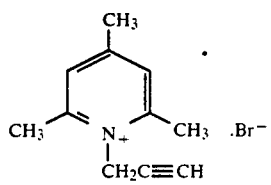 (11)
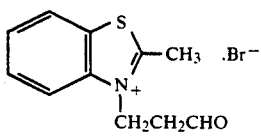 (12)
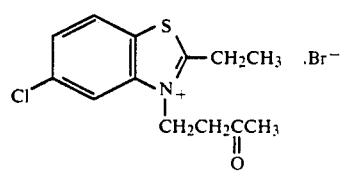 (13)
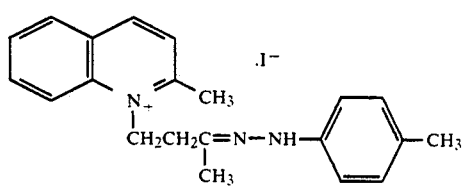 (14)
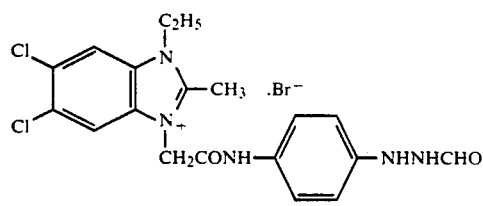 (15)
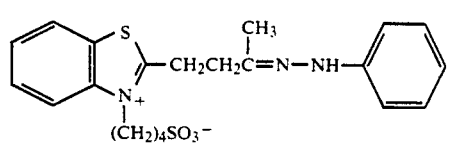 (16)
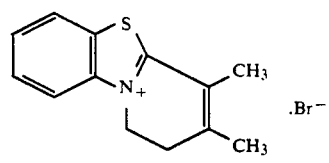 (17)
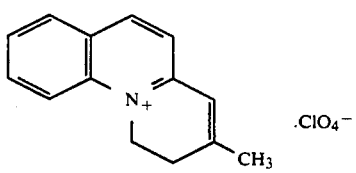 (18)
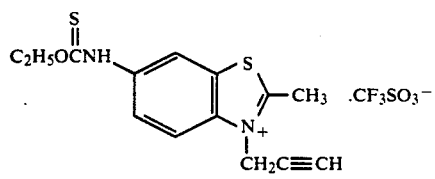 (19)
 (20)
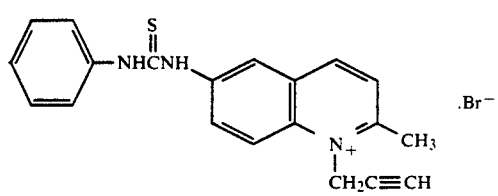 (21)
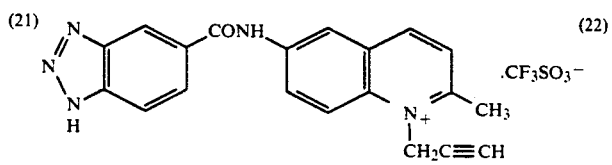 (22)

-continued
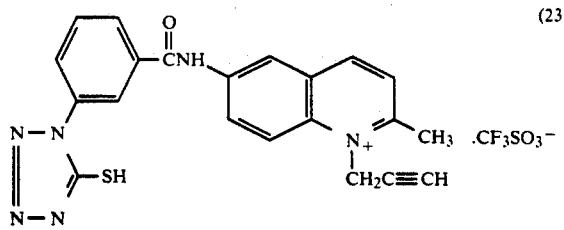(23)
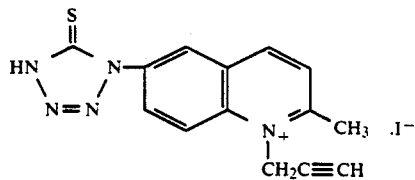(24)
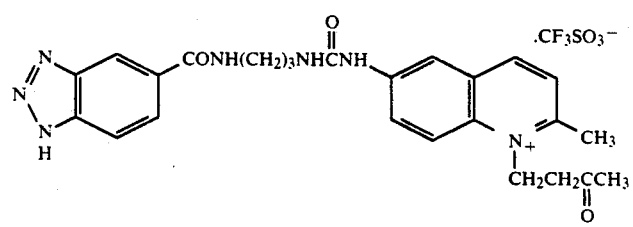(25)
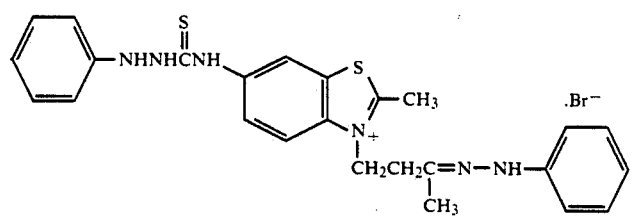(26)
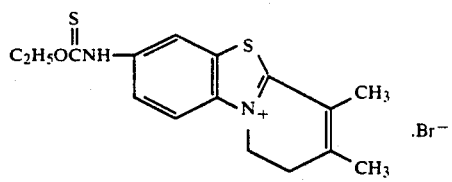(27)
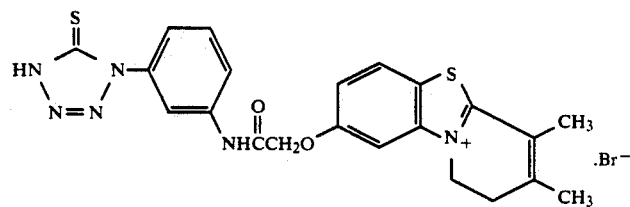(28)
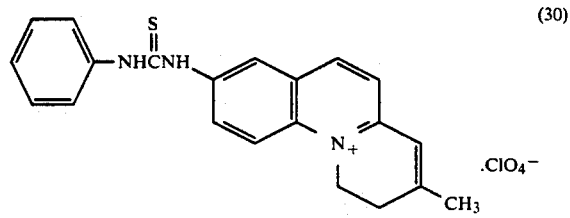(29)
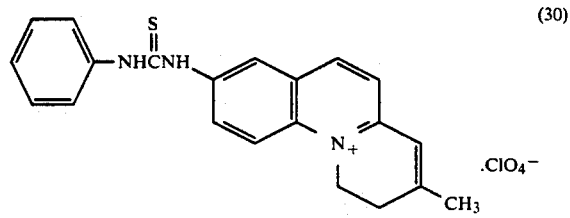(30)
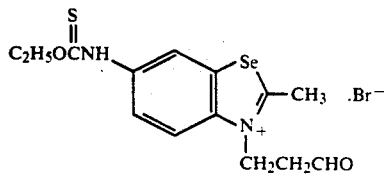(31)

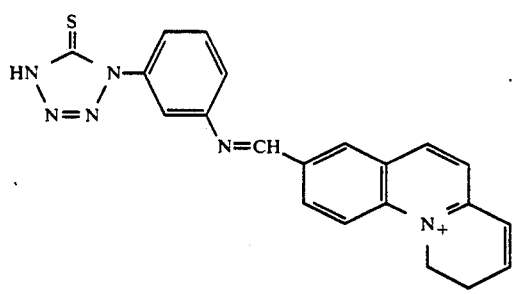

(32)

-continued

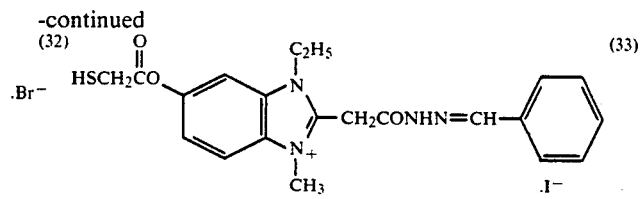

(33)

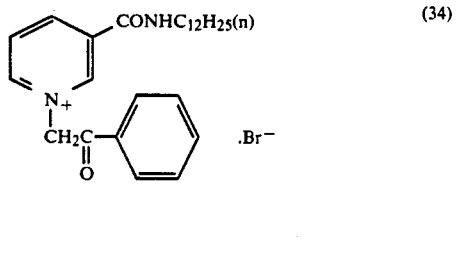

(34)

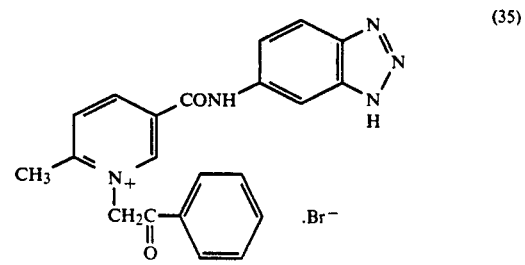

(35)

The compounds set forth above may be produced, for example, by the processes described in "Research Disclosure" No. 22534 (published in January of 1983, pp 50 to 54) and disclosed in U.S. Pat. No. 4,471,044 or by the modified processes thereof.

It is particularly preferred that the nucleating agent represented by the general formula (N-I) and used in this invention has the following characteristics (1) to (6), and it is most preferred that it has the characteristic (6).

(1) To have a substituting group $X^1$ serving as a group for promoting adsorption to silver halide.

(2) To have the characteristic (1) wherein the group $X^1$ for promoting adsorption to silver halide comprises a nitrogen-containing heterocyclic ring, such as thioamide group, heterocyclic mercapto group or a nitrogen-containing heterocyclic ring which forms imino-silver.

(3) To have the characteristic (2) wherein the heterocyclic group containing Z is quinolinium, isoquinolinium, naphtopyridinium or benzothiazolium.

(4) To have the characteristic (2) wherein alkynyl group is included as a substituting group for $R^1$, $R^2$ or Z.

(5) To have the characteristic (5) wherein $R^1$ is propargyl group.

(6) To have the characteristic (2) wherein the thioamide group of $X^1$ is thiourethane group or the heterocyclic mercapto group of $X^1$ is mercaptotetrazole (7) To have the characteristic (6) wherein $R^1$ forms a ring in combination with the heterocyclic ring containing Z.

(II-2) Particularly preferred compounds used as the structure (B) in this invention further include those represented by the following general formula (N-II) of:

$$R^{21}-N-N-G-R^{22} \quad \text{(N-II)}$$
$$\phantom{R^{21}-N}|\phantom{N}|$$
$$\phantom{R^{21}-N-N}R^{23}\ R^{24}$$

In the general formula (N-III) set forth above, $R^{21}$ stands for an aliphatic, aromatic or heterocyclic group; $R^{22}$ stands for hydrogen atom or an alkyl, aralkyl, aryl, alkoxy, aryloxy or amino group; G stands for a carbonyl, sulfonyl, sulfoxy, phosphonyl or iminomethylene (HN=C) group; and $R^{23}$ and $R^{24}$ each stands for a hydrogen atom or either one of them stands for a hydrogen atom with the other being an alkylsulfonyl, arylsulfonyl or acyl group. A hydrazone structure

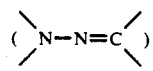

may be formed by G, $R^{23}$, $R^{24}$ and the nitrogen of hydrazine. The aforementioned groups may optionally be substituted by substituting groups.

In the general formula (N-II), the aliphatic group represented by $R^{21}$ may be a straight-chain, branched-chain or cyclic alkyl, alkenyl or alkynyl group.

Examples of the aromatic groups represented by $R^{21}$ include monocyclic or bicyclic aryl groups, such as phenyl groups and naphthyl group.

Examples of the heterocyclic ring represented by $R^{22}$ are three- to ten-member saturated or unsaturated heterocyclic rings containing at least one of N, O and S atoms, and may be monocyclic rings or may form condensed rings with other aromatic or heterocyclic rings. Preferable heterocyclic rings include five-member or six-member aromatic heterocyclic rings, the specific examples being pyridinyl group, quinolinyl group, imidazolyl group and benzimidazolyl group.

$R^{21}$ may be substituted by a substituting group. The substituting group may be selected from those which will be set forth below, and may have a further substituting group or groups.

Examples of the substituting group are alkyl groups, aralkyl groups, alkoxy groups, alkyl or aryl groups, substituted amino groups, acylamino groups, sulfonylamino groups, ureido groups, urethane groups, aryloxy groups, sulfamoyl groups, carbamoyl groups, aryl groups, alkylthio groups, arylthio groups, sulfonyl groups, sulfinyl groups, hydroxy groups, halogen atoms, cyano groups, sulfo groups and carboxy groups. These groups may be connected to form a ring.

It is preferable that $R^{21}$ is an aryl group, an aromatic heterocyclic ring or a methyl group substituted by an aryl group, and more preferably $R^{21}$ is an aryl group.

When G is a carbonyl group, is preferably selected from a hydrogen atom, alkyl groups (such as methyl, trifluoromethyl, 3-hydroxypropyl, 3-methanesulfonamidopropyl groups), aralkyl groups (such as o-hydroxybenzyl group), and aryl groups (such as phenyl, 3,-5-dichlorophenyl, o-methanesulfoneamidophenyl, 4-methanesulfonylphenyl groups). A hydrogen atom is particularly preferable.

When G is a sulfonyl group, $R^{22}$ is preferably selected from alkyl groups (such as methyl group), aralkyl groups (such as o-hydroxyphenylmethyl group), aryl groups (such as phenyl group) and substituted amino groups (such as dimethylamino group).

$R^{22}$ may be substituted by the substituting groups set forth hereinbefore as the substituting groups for $R^{21}$, and may also be substituted by any of acyl groups, acyloxy groups, alkyloxycarbonyl groups, aryloxycarbonyl groups, alkenyl groups, alkynyl groups or nitro groups.

These substituting groups may be further substituted by the substituting groups, and may form a ring by inter-connection.

It is preferred that or $R^{21}$ or $R^{22}$, particularly $R^{21}$, has an anti-dispersion group, a so-called balast group, such as a coupler. The balast group has 8 or more carbon atoms, and comprises one or a combination of alkyl groups, phenyl groups, ether groups, amide groups, ureido groups, urethane groups, sulfonamide groups and thioether groups.

$R^{21}$ or $R^{22}$ may have a group $X^2\text{-}(L^2)_{m_2}$ which promotes adsorption of the compound represented by the general formula (N-II) to the surfaces of silver halide grains. In the formula $X^2\text{-}(L^2)_{m_2}$, $X^2$ is the same as $X^1$ in the general formula (N-I), and may be preferably selected from thioamide groups (except thiocarbazide and derivatives thereof), mercapto groups and five-member and six-member nitrogen-containing heterocyclic groups. $L^2$ stands for a divalent linking group, and is selected from those referred to as $L^1$ in the general formula (N-I). $m_2$ is zero or 1.

More preferably, $X^2$ is a cyclic thioamide group, IO (i.e a mercapto-substituted nitrogen-containing heterocyclic ring such as 2-mercaptothiadiazole group, 3-mercapto-1,2,4-triazole group, 5-mercaptotetrazole group, 2-mercapto-1,3,4-oxadiazole group or 2-mercaptobenzoxadiazole group), or a nitrogen-containing heterocyclic group (such as benzotriazole group, benzimidazole group or indazole group).

The most preferable for $R^{23}$ and $R^{24}$ is a hydrogen atom.

The most preferable group for G in the general formula (N-II) is carbonyl group.

More preferably, the compound represented by the general formula (N-II) has an adsorption group to be adsorbed by silver halide grains. Particularly preferred adsorption groups are mercapto groups, cyclic thioamide groups and ureido groups as described for the adsorption groups for the compounds represented by the general formula N-I).

Specific examples of the compounds represented by the general formula (N-II) will now be set forth below.

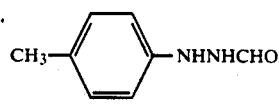

(36)

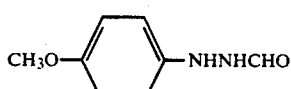

(37)

(38)

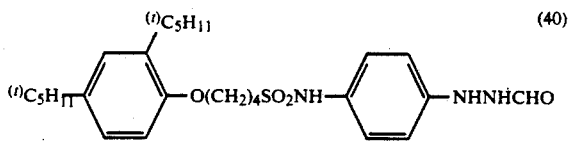

(39)

(40)

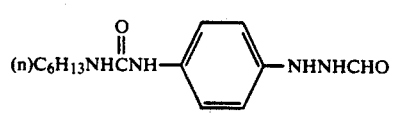

(41)

(42)

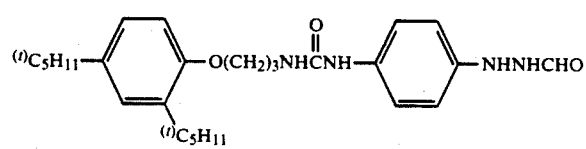

(43)

-continued
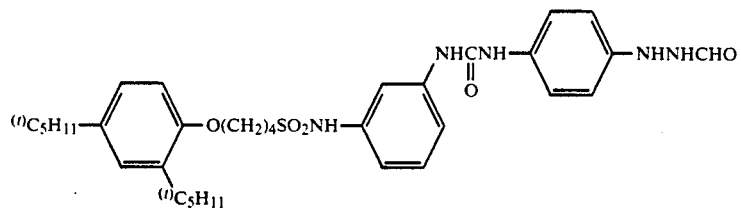
(44)
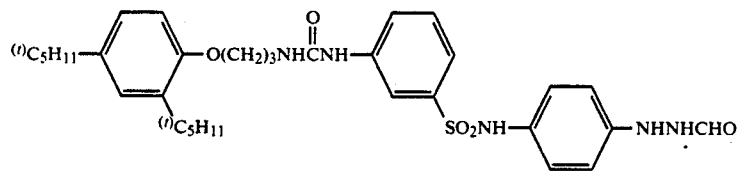
(45)
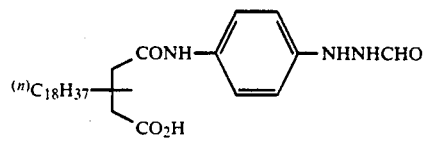
(46)
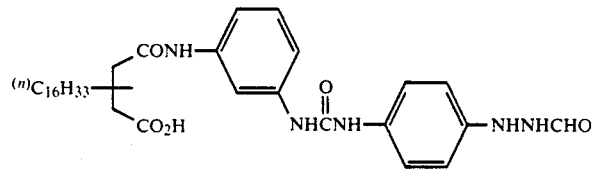
(47)
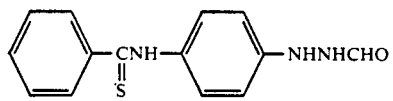
(48)
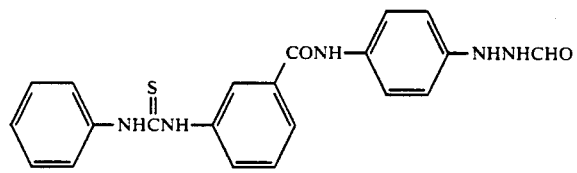
(49)
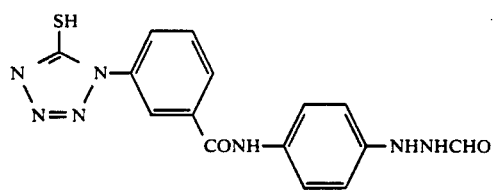
(50)
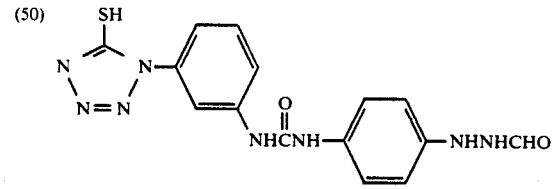
(51)
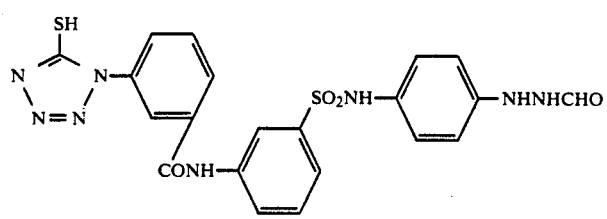
(52)
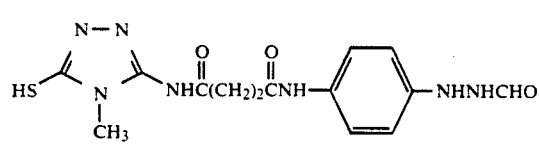
(53)

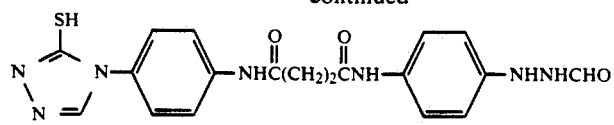 (54)
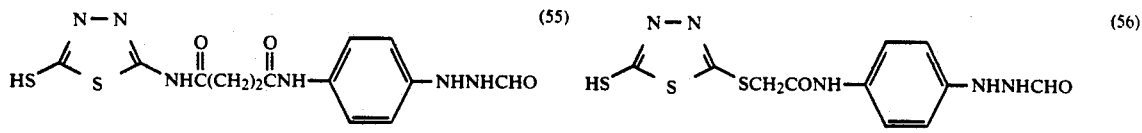 (55) (56)
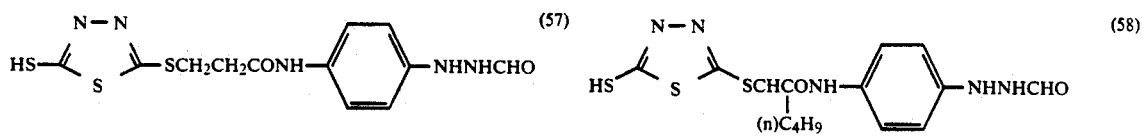 (57) (58)
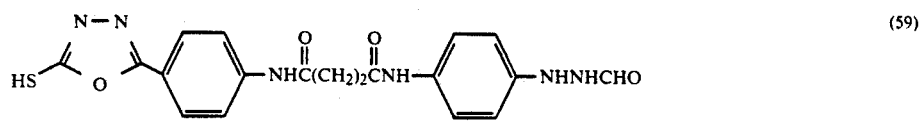 (59)
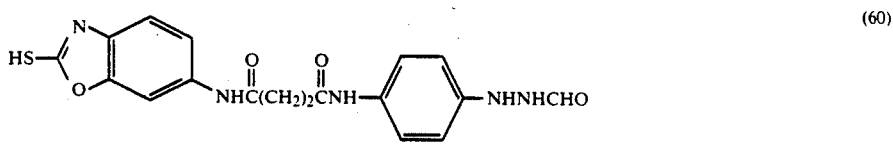 (60)
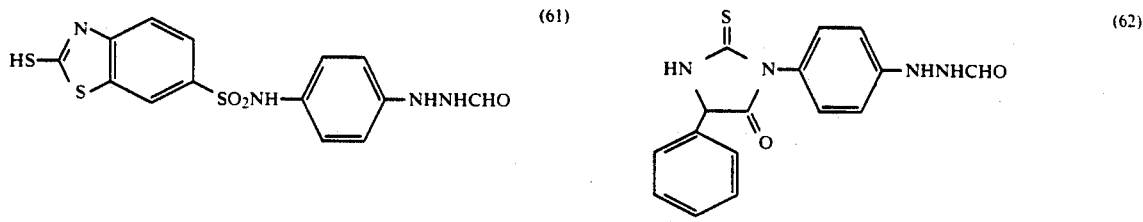 (61) (62)
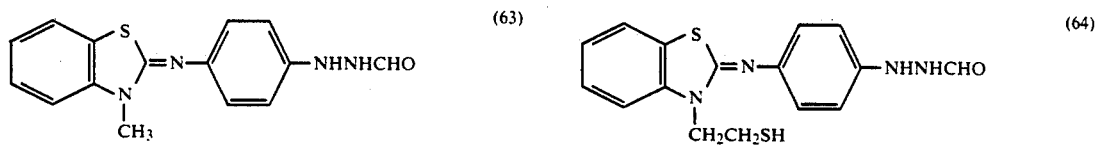 (63) (64)
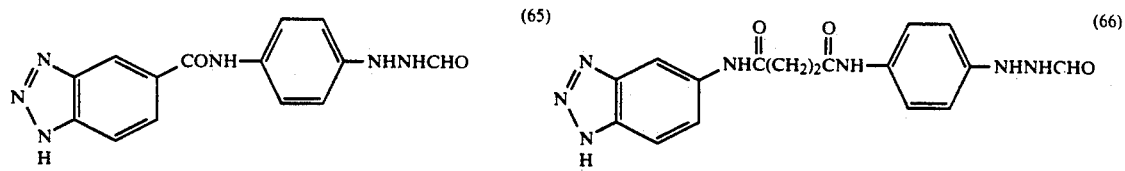 (65) (66)
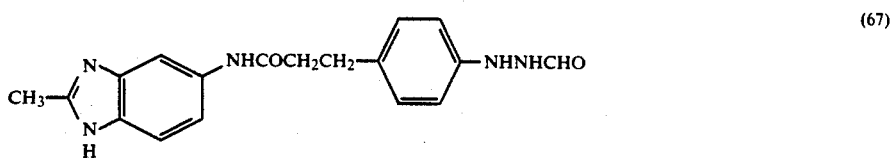 (67)
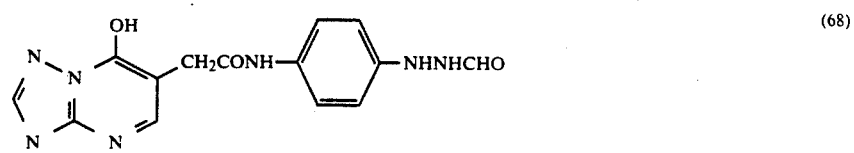 (68)

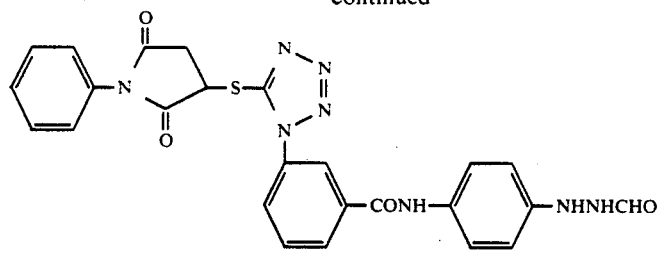(69)

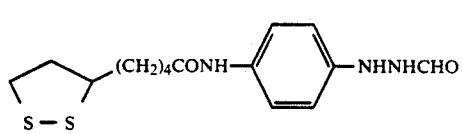(70)

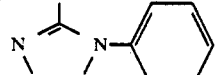(71)

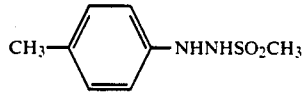(72)

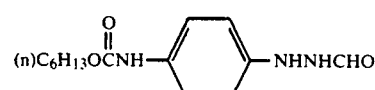(73)

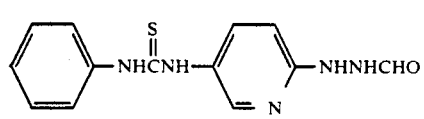(74)

(75) $(n)C_{12}H_{25}NHNHCHO$

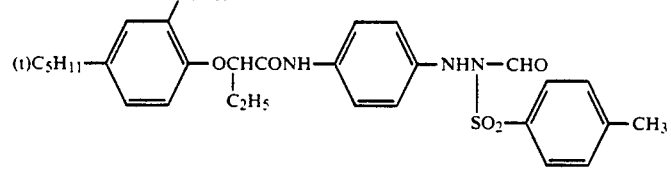(76)

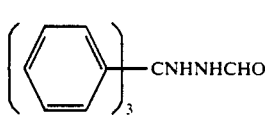(77)

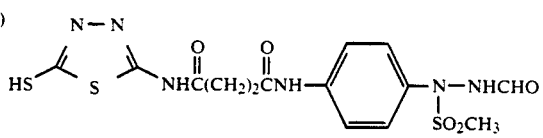(78)

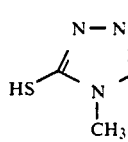

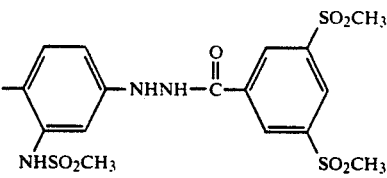(79)

The compounds represented by the general formula (N-II) may be synthesized, for example, by the processes disclosed in the patent specifications referred to in "Research Disclosure", No. 15162 (November of 1976, pp 76 to 77), ibid, No. 22534 (January of 1983, pp 50 to 54) and ibid, No. 23510 (November of 1983, pp 346 to 352) or the processes disclosed in U.S. Pat. Nos. 4,080,207, 4,269,924, 4,273,364, 4,278,748, 4,385,108, 4,459,347, 4,478,928 and 4,560,638, British Patent No. 2,011,391B and Unexamined Japanese Patent publication No. 179734/1985 (EP 0,154,293A).

Meanwhile, the nucleating agent represented by the general formula (N-II) has preferably the following characteristics (1) to (7), and it is most preferable that it has the characteristic (7).

(1) To have a substituting group $X^2$ which promotes adsorption to silver halide grains.

(2) To have the characteristic (1) wherein the group $X^2$ for promoting adsorption to silver halide grains is a heterocyclic mercapto group or a nitrogen-containing heterocyclic ring which forms imino-silver.

(3) To have the characteristic (2) wherein the group represented by G-$R^{22}$ is formyl group.

(4) To have the characteristic (3) wherein the groups $R^{23}$ and $R^{24}$ are hydrogen atoms.

(5) To have the characteristic (3) wherein the group $R^{21}$ is an aromatic group.

(6) To have the characteristic (3) wherein the group $R^{21}$ has ureido group as a substituting group.

(7) To have the characteristic (2) wherein the heterocyclic mercapto group represented by $X^2$ is 5-mercaptotetrazole or 5-mercapto-1,2,4-triazole.

Other nucleating agents which may be used as the structure (B) in this invention will be set forth below.

(i) Hydrazone compounds represented by the following general formula of:

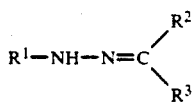

wherein $R^1$, $R^2$ and $R^3$ each stands for an alkyl group, an aryl group, a heterocyclic ring, an acyl group, a sulfonyl group, an alkoxycarbonyl group or a derivative thereof.

Specific examples of hydrazone compounds are 2-(2-isopropylidene-hydrazino)phenyl isothiocyanate or the like described, for example, in U.S. Pat. Nos. 3,227,552 and 3,615,615, Unexamined Japanese Patent Publication No. 3426/1977 (U.S. Pat. No. 4,094,683) and Japanese Patent Publication No. 1416/1976.

(ii) Aldehyde compounds represented by the following general formula of:

wherein R is the same as each of the groups $R^1$, $R^2$ or $R^3$ defined above.

Specific examples of aldehyde compounds are represented by the following formula of:

These aldehyde compounds are disclosed, for example, in Unexamined Japanese Patent publication No. 9678/1972 and Japanese Patent Publication Nos. 19452/1977 and 20088/1974.

(iii) Metal hydride compounds disclosed, for example, in Japanese Patent Publication No. 28065/1970, U.S. Pat. Nos. 3,951,665 and 3,804,632 and British Patent No.

(iv) Dihydro compounds disclosed, for example, in U.S. Pat. No. 3,951,656, Belgian Patent No. 708,563, German Patent Nos. 1.572,125 and 2,104,161 and German Patent Application OLS No. 1,572,140. These compounds may also be employed in this invention.

Structure (C) It is essential that the catalytically affected adsorbing structure (C) has the following two characteristics.

(1) An adsorbent specifically adsorbing the structure (C) with a high bonding strength is available.

(2) When the synthetic substrate (B)-(A)-(C) including the structure (C) is reacted with an enzyme, the resultant reaction product ((B)-(A')) does not include the structure (C). This characteristic depends on the characteristic of the structure (A) or the reaction mode of the enzyme. Also, this characteristic depends on the bonding mode of the structure (C) to the structure (A) so that it is satisfied by selecting a proper functional group participating in the bonding or by binding the structure (C) to the structure (A) through a spacer group. Details in this connection are described in the section describing the linkage of structure (B)-(A)-(C).

Since the structure (C) is introduced in the synthetic substrate, it is desirable that the structure (C) has a molecular weight of not higher than about 1000.

Examples of the effective structure (C) are vitamins or hormones when combinations of vitamins or hormones with vitamin receptors or hormone receptors are used, antigens (particularly haptens) when the combinations of antigens with antibodies are used, and coenzymes when the combinations of enzymes with coenzymes are used. Among the combinations described above, particularly effective combinations are combinations of vitamins with corresponding receptor proteins, and the combinations of haptens with corresponding antibodies.

The index for effectiveness is the association constant in a specific combination. For example, it is more preferable that the association constant $K_a$ between the structure (C) and the corresponding specific adsorbent is large enough to adsorb most or all of the unrelated synthetic substrate in a limited treating time. If the unreacted synthetic substrate is left in the separated reaction product of the enzymatic reaction even after the separation by the use of an adosrbent, the contaminating unreacted synthetic substrate acts as a source of noise (background). However, when the association constant $K_a$ is sufficiently large, the quantity of the unreacted synthetic substrate which is not adsorbed by the adsorbent is low enough within a limited treating time so as not to cause noise (background) at the subsequent photochemical determination step.

When the structure (C) is biotin and avidin immobilized by agarose beds (hereinafter referred to simply as "avidin-agarose") is used as the adsorbent, the association constant ($K_a$) between the biotin and avidin is $10^{15}$ (M). Accordingly, using avidin-agarose in an amount several times as large as the molecular equivalent of biotin contained in the used synthetic substrate, the concentration of the unadsorbed synthetic substrate can be easily depressed below the detection limit ($10^{-10}$ mole/l).

The combination of the adsorbent and the structure (C) may be comprised of an antigen and an antibody. However, it is desirous that the $K_a$ of each combination should be as large as possible, preferably $K_a > 10^9$, more preferably $K_a > 10^{10}$, to achieve the object of this invention. Although the effectiveness can be improved by increasing the relative added amount of the adsorbent when a combination having a small $K_a$ is used, it is recommended to use the combination having a high $K_a$, since the quantity or concentration of the unreacted synthetic substrate left unadsorbed by the adsorbent reaches a level higher than the limit for photographic determination to raise the background density if the association constant $K_a$ is too low. By passing the sample through a column packed with an adsorbent, similar to the adsorption chromatography, a trace enzyme can be measured since separation can be effected even though the quantity of used adsorbent is small.

Anyway, the quantity of the used adsorbent varies depending on the association constant $K_a$ of the adsorption reaction and the reaction method, the actually used quantity of the adsorbent relative to the quantity of the used synthetic substrate is set so that no background is photographically detected.

Linkage of Structure (B)-(A)-(C)

The synthetic substrate used in this invention is composed of at least one of the photographically active labelling structure (B) and at least one of the structure (C) having a specific adsorption charactristic, which are linked with each other through at least one of the structures (A) corresponding to the substrate specificity of an enzyme.

The structure (B) and the structure (A) are linked with each other directly or through a linking group (D), and likewise the structure (C) and the structure (A) are linked with each other directly or through a linking group (D). The conditions required for linking are:

(1) the enzyme activity should not be inhibited by the linking;

(2) the structure (C) is released by an enzymatic reaction; and (3) the photographic activity of the structure (B) should not be lost by the linking.

The site of cleavage by an enzymatic reaction is:
(i) structure (A) itself,
(ii) the linkage between the structures (B) and (A),
(iii) the linking group (D) itself between the structures (B) and (A),
(iv) the linkage between the structure (A) and (C), or
(v) the linking group (D) itself between the structures (A) and (C).

These conditions may be satisfied by selecting proper functional groups which participate information of the linkages between the linking group (D) and the respective structures (A), B) and (C).

The latter-mentioned condition, i.e. the photographic activity should not be lost, includes the use of precursors which recover the necessary properties upon contact with silver halide or at the developing step. The linking groups which provide precursors are disclosed in Unexamined Japanese Patent Publication Nos. 93442/1984 (U.S. Pat. No. 4,522,917), 201057/1984 (EP 0,125,523A), 218439/1984 (U.S. Pat. No. 4,554,243), 219741/1974, 41034/1985 (U.S. Pat. No. 4,618,563), 43739/1986 (U.S. Pat. No. 4,659,651) and 95346/1986 (U.S. Pat. No. 4,690,885). The linking groups (D) may include an amino acid, peptide polyamino acid, monosaccharide, disaccharide, polysaccharide (oligomer or polymer), nucleic acid base nucleotide, nucleoside, polynucleoside or polynucleotide. The linking is effected via functional groups on structure (A) (e.g. an amino group, an imino group, a carboxy group, a hydroxy group, a sulfhydryl group, or a group capable of reacting with these groups) and functional groups on the photographically active labelling structure (B) (e.g. an amino group, an imino group, or a group capable of reacting with these groups). These functional groups may exist in each structure or may be introduced into each structure by the chemical reaction therewith of a compound containing such a group. Further, these functional groups may be employed singly or in combination.

On the other hand, which is the compound as the linking group having a group capable of reacting with the aforesaid funtional groups on the structures (A) and (B), there are the following compounds: alkyl chloroformates (e.g. diethyl chloroformate, isobutyl chloroformate, etc.), aldehydes (e.g. formaldehyde, glutaraldehyde, etc.), isocyanates (e.g. xylene diisocyanate, tolylene diisocyanate, hexamethylene diisocyanate, etc.), thiocyanates (e.g. xylylene thioisocyanate, etc.), vinyl compounds (e.g. divinyl ketone, methylene bisacrylamide, divinyl sulfone, etc.), active halides (e.g. cyanuric chloride, mucohalogenic acids, nitrophenyl chloride, phenol-2,4-disulfonyl chloride, etc.), active esters (e.g. p-toluenesulfonic acid succinyl ester, etc.), imidazolic acid amides (e.g. carbonyl diimidazole, sulfonyl diimidazole, triimidazolyl phosphate, etc.), pyridinium compounds (e.g. N-carbamoyl pyridinium, N-carbamoyloxypyridium, etc.), sulfonic acid esters (e.g. alkanesulfonic acid esters, etc.), bismaleimides (e.g. N,N'-(1,3-phenylene)bismaleimide, etc.), diazonium compounds (e.g. bisdiazobenzidine, etc.), epoxy compounds (e.g. bisoxirane, etc.), acid anhydrides, carboxylic acids and ethyleneimines.

Further, for linking the structure (A) and structure (B) or (C) directly or through the linking group (D), for example, a carboxy group among the aforesaid functional groups of the respective structures is activated by a carbodiimide (e.g. 1-ethyl-3-(3-dimethylaminopropyl)carbodiimide, 1-cyclohexyl-3-(2-morphodinyl-4-ethyl)carbodiimide, N,N'-dicyclohexylcarbodiimide, etc.), and isoxazolium, a pseudo base, an active ester (e.g. benzenesulfonic acid hydroxysuccinimide ester, etc.), an alkyl chloroformate (e.g. isobutyl chloroformate, etc.), and then a linking may be formed between the activated group and the functional group of the other structure to be reacted.

With respect to the manner of a linking made between the functional group of the structure (A) having specificity for an enzyme and the funnctional group of the photographically active labelling structure (B) or the structure (C) having specific adsorption characteristic or between each of the functional groups and the functional groups of the linking group (D), there are:

(1) linking by direct reaction of the functional groups with each other;

(2) cross-linking by a compound having two or more active functional groups; and (3) linking formed by activating one of these functional groups using an activator and introducing the activated group to the other functional group (e.g. an amino group, a sulfhydryl group, etc.).

It is desirable that the reactions for linking the three functional parts (i.e. the structures (A), (B) and (C)) directly or through the linking group (D) be performed successively.

Each linking reaction should be performed while using the respective components mixed in a molar ratio of from 1/100 to 100/1, preferably from 1/30 to 30/1, more preferably from 1/10 to 10/1.

The reactivities of respective groups and the reaction methods are described in detail, for example, in SEIKAGAKU JIKKEN KOZA(Lectures on Biochemical Experiments) vol. 1, entitled "Chemistry of Proteins", vol. 2, entitled "Chemistry of Nucleic Acids", vol. 3, entitled "Chemistry of Lipids", and vol. 4, entitled "chemistry of Glucosides", all edited by Biochemical Association, Japan, published by Tokyo Kagaku Dojin, 1976; and PEPTIDE SYNTHESIS, by Izumiya et al., published by Maruzen Publishing Co., Ltd., 1975.

Method of Measurement

The basic steps for carrying out the method of measurement using the synthetic substrate of this invention will be described in brief.

Step 1: A synthetic substrate prepared according to the invention is allowed to contact with a sample containing the enzyme to be measured under predetermined conditions for enzymatic reaction.

Step 2: All or a portion of the reaction liquid from the aforesaid enzymatic reaction is taken up and allowed to contact with an adsorbent specifically adsorbing the structure (C) and immobilized by a carrier so as to separate the reaction product from the unreacted synthetic substrate.

Step 3: Either one of the reaction product or the unreacted synthetic substrate separated from one another at the Step 2 is allowed to contact with silver halide (in an emulsion form or a film coated with an emulsion), followed by development.

Step 4: The optical density of the developed silver and/or colored dye is measured.

Step 5: Comparing the thus measured optical density with the optical density of a preliminarily drawn calibration curve to find the quantity of the enzyme contained in the sample.

The method of this invention can also be utilized for the activity measurement and determination of enzymes, when the enzymes are used as the label markers in enzyme immunoassay processes. Enzyme immunoassay is a method of detecting and determining at high sensitivity trace components in the living body or trace drugs, utilizing a specific binding mode of an antigen-antibody reaction and the catalytic action of enzymes in combination. In other words, in an enzyme immunoassay, after binding an enzyme to an antigen or antibody, the extent of the antigen-antibody reaction is detected using the enzyme activity as a labelling substance and the amount of the antigen or antibody is determined based thereon. Such measurement systems are generally classified as follows: the case where the antigen and/or antibody is to be measured; the case where an enzyme-labelled antigen (or antibody) is competitive or not competitive with an enzyme-labelled antibody (or antigen), and the case where a lebelled antigen (or antibody) is competitive with an unlabelled antibody (or antigen), the antigen-bound antibody is separated or not separated from the unbound antigen or antibody prior to measurement. Of these methods, typical methods include (1) a solid phase method, (2) a double antibody method, (3) a homogenous system enzyme immunoassay, and (4) a sandwich method. Details of these methods are described, for example, in Wisdom, Clin. Chem, vol. 22, 1243 (1976); A. Voller et al., The Enzyme Linked Immunosorbent Assay, published by Flowing Publications, Guerney, Europe (1977); M. J. O'Sullivan et al., Annals of Clinical Biochemistry, vol. 16, 221 (1979); Kiyoshi Miyai, Enzyme Immunoassay, Clinical Test, vol. 22, No. 11, extra edition in 1978; and Eiji Ishikawa, Tadashi Kawai and Kiyoshi Miyai, KOSO MEMEKI SOKUTEIHO (Enzyme Immunoassay), published by Igaku Shoin, 1978.

By the application of the method of this invention for activity measurement of an enzyme labelled to an antigen or antibody, the enzyme activity can be assayed at higher sensitivity and with greater safety than with conventional methods, whereby the sensitivity and the accuracy of the immunoassay is enhanced.

According to the method of this invention, a plurality of enzymes contained in a test sample can be discriminatively and/or simultaneously detected. That is, as a specific method for discriminatively assaying two or more enzymes, there is a method wherein a substrate fitting only one kind of enzyme among a plurality of enzymes is used utilizing the specificity of the enzyme, a method wherein a substrate is endowed with the specificity to an enzyme by controlling the reaction conditions (e.g. reaction pH, reaction temperature, ionic strength, etc.), a method wherein the measurement of an enzyme is performed in the presence of inhibitors or inactivators specific to enzymes other than the enzyme to be measured, and a method comprising a combination of these methods.

The term "inhibitor" used herein refers to a material which inhibits the function of the enzyme by a reversible change while the term "inactivator" refers to a material which inhibits and inactivates the function of the enzyme by an irreversible change. The inhibitor and the inactivator to each enzyme are described along with the specificity in DATABOOK OF BIOCHEMISTRY, first and second separate volumes, edited by the Biochemical Association, Japan, published by Tokyo Kagaku Dojin, 1979 and 1980; and The Enzyme, P. D. Boyer, vols. 3, 4 and 5 (1971), Academic Press, New York, etc.

Further, as practical methods for simultaneously measuring two or more enzymes discriminatively, there are, for example, the methods described below:

(1) A method which comprises measuring the total activities of all enzyme components, with the progress of the reaction, after a certain period of time, using a synthetic substrate having common specificities to two or more enzymes and simultaneously adding an inhibitor or inactivator acting specifically to only one component of the plural enzyme components, and repeating the above procedure in accordance with the number of the enzyme components to thereby determine the activity of the respective enzyme components from the difference between the total activities before the addition of the inhibitor or inactivator and the activities after the addition thereof at each measured time;

(2) A method which comprises performing enzyme reactions using a plurality of sythetic substrates different from each other, each of which corresponds, in unitary reaction, to each enzyme in the plural enzymes to be measured and each of which form nucleating structure (B)-containing product having a different structure from any other product or products by an enzyme reaction, either each nucleating structure (B)-containing product or the unreacted synthetic substrate corresponding to each enzyme being separated by an appropriate separation method (e.g. liquid chromatography, etc.) utilizing differences in physiochemical properties between the plural nucleating structure (B)-containing reaction products and/or plural unreacted synthetic substrates and then being brought into contact with silver halide, whereafter one develops the separated products or synthetic substrate separtely by the number of the enzymes and separately measures densities of the developed silver and/or colored dyes, thereby determining the activity of each enzyme; and (3) A method comprising a combination of the above-described methods.

In any mode of the method of this invention described above, it is convenient to employ, if desired or necessary, such a method that after stopping the enzyme reaction using appropriate conditions to stop the enzyme reation using appropriate conditions to stop the enzyme reation (e.g. by increasing or decreasing the reaction pH, or by elevating or lowering the reaction temperature, etc.), or, using an enzyme inhibitor or inactivator or a modifier (e.g. urea, guanidine hydrochloride, or a surface active agent having a modifying action such as SDS, etc.) which is also an inactivator in a broad sense, either the reaction product containing nucleating structure (B) or the unreacted synthetic substrate is brought into contact with silver halide.

More specific means for assaying either the nucleating structure-containing reation product formed by the enzyme reaction or the unreacted synthetic substrate by brining it into contact with silver halide in accordance with this invention include:

(1) a liquid containing the above-described component is dropped onto a silver halide photographic emulsion containing unexposed silver halide grains and absorbed on the grains. The mixture is placed in a transparent cell, and a developer for photographic use is added to the mixture followed by development to blacken the mixture. Thereafter, optical density is measured (contact in solution).

(2) At least one silver halide emulsion layer containing unexposed silver halide grains is formed on a support, and a liquid containing the above-described component is dropped onto the emulsion layer to thereby allow the liquid to permeate into the emulsion layer and adsorb onto the silver halide grains in the emulsion layer. Then, the emulsion layer is immersed in a photographic developed as in ordinary development processing to blacken the developed silver, and then optical density blackened at the spotted area is measured (contact onto film).

Among the above-described means, means (2) is particularly preferred and is convennient for assaying a plurality of enzymes. That is, a plurality of reaction products containing nucleating agent structures (B) or plural unreacted synthetic substrates are separated from each other, spotted or dropped on the emulsion layer by at least the number of enzymes to be measured, each spot is immersed in a developer to blacket the spot or drop portions, and blackening optical density or the degree thereof is then measured.

For practicing the method of this invention, in a more preferred embodiment, an analysis element used for the method of this invention comprises an auxiliary layer formed under a silver halide-containing layer to increase the amount of spotted test liquid absorbed. The function of the auxiliary layer referred to herein is to accelerate absorption of the spotted test liquid into the layer and increase the uptake of the aforesaid enzyme to be measured, whereby the amount to be adsorbed onto silver halide grains is increased. Such an auxiliary layer is composed of a porous membrane, a filter paper, a filter, gelatine and/or a polymer and has a thickness of 1 $\mu$m to 100 $\mu$m, preferably 3 $\mu$m to 40 $\mu$m. This auxiliary layer can also contain, in addition to gelatin or a polymer, silver halide or additives for ordinary silver halide light sensitive materials, e.g. an antifoggant, a dye, a surface active agent, colloidal silver, etc.

Gelatin used in this invention, as a binder for silver halide or in other layers, is ordinary lime-treated gelatin, acid-treated gelatin, enzyme-treated gelatin, a gelatin derivative obtained by chemically modifying gelatin, such as phthalated gelatin, or graft gelatin obtained by graft polymerizing a monomer in the presence of gelatin. Such gelatin may be used alone or as a mixture thereof in an appriate proportion. As polymers used in this invention, polymers which are liable to swell or dissolve in water are preferred, examples of which include albumin, agar, gum arabic, alginic acid, a hydrophilic homopolymer of copolymer of a polymerizable vinyl monomer such as vinyl alcohol, vinyl pyrrolidone, acrylamide, acrylic acid, methacrylic acid, styrenesulfonic acid, styrene, methyl methacrylate, a cellulose compound (e.g. hydroxyethyl cellulose, carboxymethyl cellulose, dextrin, etc.) water soluble starch, etc. If necessary or desired, a hardening agent may be added to the polymer for insolubilizing the polymer.

The silver halide which may be used in this invention include silver chloride, silver bromide, silver iodobromide, silver chlorobromide, silver chloroidide, silver chloroiodobromide.

The silver halide emulsion which may be used in this invention include a surface latent type emulsion or an internal latent type emulsion. The silver halide emulsion may be a so-called coacervative emulsion wherein the phase internally of each grain is different from the phase on the surface of each grain. The crystal habit of the silver halide grains may be any of cubic, octahedron, tetradecahedron or plate shape having high aspect ratio.

Silver halide(s) contained in a photographic emulsion used in the present invention can be prepared in a conventional manner, e.g. by a single jet method, a double jet method, or a combination thereof. Useful preparation methods of silver halide emulsions are described, for example, in Trivelli and Smith, The Photographic Journal, vol. 79, pp 330 to 338 (1939), C. E. K. Mees, The Theory of The Photographic Process, 1966, published by MacMillian, Glafkides, Photographic chemistry, vol. I. pp 327 to 336, published by Fountain Press, etc.

The grain size of silver halide(s) in an emulsion(s) employed in this invention is conventional or smaller. It is thus generally preferred that the average grain diameter be 0.04 to 4 microns (e.g. by measurement of number average by the projected area method). Further, the size distribution of silver halide grains in a silver halide emulsion is as narrow as possible. For this reason, silve halide grains may be formed by a double jet method or a conversion method, a so-called controlled double jet method for forming silver halide grain-forming mixture.

The silver halide emulsions employed in this invention may not be chemically ripened but generally may be chemically sensitized in a conventional manner, for example by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthiocarbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Patent No. 981,470, Japanese Patent Publication No. 6475/1956 and U.S. Pat. No. 2,716,062, etc.; and polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,065, etc.; urazoles as described in U.S. Pat. No. 3,287,135, etc.; sulfocatechols as described in U.S. Pat. No. 3,236,652, etc.; oximes as described in British Patent No. 623,448, etc.; mercaptotetrazoles; nitron; nitroindazoles as described to U.S. Pat. Nos. 2,403,927, 3,266,897 and 3,397,987, etc.; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g. hydroquinones, catechols, aminophenols, 3-pyrazolidones, ascorbic acid or derivatives thereof, reductones, phenylenediamiens, etc.), or combinations of these developing agents. The developing agents can be incorporated into a light sensitive emulsion and/or other suitable layers (e.g. a hydrophilic binder layer) of a photographic element. The developing agents can be incorporated using a suitable solvent or in the form of a dispersion as described in U.S. Pat. No. 2,592,368 or French Patent No. 1,595,778.

When a light sensitive film containing the developing agent in a coated layer or layers is used, the film is processed, after light exposure, with an ordinary photogrphic developer and in this case a so-called alkali activator, i.e. an ordinary photographic developer composition from which a developing agent component is removed may be used.

In this invention, as a binder for the silver halide emulsion layer coated on a support, ordinary gelatin (i.e. alkali-treated gelatin or acid-treated gelatin) is usually used. Furthermore, the gelatin may be partially or wholly replaced with another film-forming high molecular weight material. As such a high molecular weight material, there are used materials which do not have a harmful influence on the light sensitive silver halide emulsion, such as albumin, agar, gum arabic, alginic acid, acylated gelatin (e.g. phthalated gelatin, malonated gelatin, etc.), a homopolymer or hydrophilic vinyl compound (e.g. vinyl alcohol, vinylpyrrolidone, acrylamide, styrenesulfonic acid, acrylic acid, etc.), or copolymers containing these vinyl compounds, cellulose compounds (e.g. hydroxyethyl cellulose, carboxymethyl cellulose, dextrin, etc.), water-soluble starch, etc. Other layers (e.g. a filter layer, subbing layer, etc.) than the silver halide emulsion layer may contain such a film-forming high molecular weight material as in the silver halide emulsion layer.

The development performed in this invention can be by the following manner. That is, when a silver halide emulsion is formed on a support, a development process as is conventionally used for the development of photographic materials can be used. Also, the photographic development can be performed by spreading, coating, impregnating or spraying a photographic developing composition onto the silver halide emulsion layer formed on the support. Furthermore, when the silver halide emulsion is in the liquid state, photographic development can be performed by mixing the emulsion with a liquid developing composition.

The silver halide emulsion layer contacted with the nucleating agent as described above is processed by a conventional photographic processing. A known processing solution can be used in this case. The processing temperature is usually selected from 18° C. to 50° C. but may be lower than 18° C. or higher than 50° C.

With an increase in developing temperature, photographic density increases. Therefore, it is usually preferred to process at a pre-determined constant temperature. However, in place of processing at a constant temperature, a process may be employed wherein changes in photographic density due to changes in developing temperature are substantially prevented by using a neutralizing layer and a temperature compensation polymer layer. For example, the development can be performed on a silver halide emulsion layer formed adjacent to a combined layer of an acid polymer layer as described in U.S. Pat. Nos. 4,056,394 and 4,061,496 and Unexamined Japanese Patent Publication No. 72622/1978 (U.S. Pat. No. 4,199,362).

Developing solutions used in the case of black-and-white photographic processing can contain known developing agents. As such developing agents, dihydroxybenzenes (e.g. hydroquinone), 3-pyracolidone (e.g. 1-phenyl-3-pyrazolidone), aminophenols (e.g. N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents viscosity-imparting agents, etc.

As a special aspect of development, a developing method which comprises treating a light sensitive material in which a developing agent is contained, e.g. in an emulsion layer, in an aqueous alkaline solution can be used. Of such developing agents, a hydrophobic type can be incorporated into an emulsion layer by latex dispersion, as disclosed in Research Disclosure, No. 169, RD-16928. Such development processing can also be used in combination with silver salt stabilization, e.g. with a thiocyanates(s).

In place of the above-described black-and-white development process, a color development as is used in ordinary color photographic process can also be performed. In this case, a coupler is preliminarily dissolved in the developer or incorporated in the silver halide emulsion layer of a light sensitive element (see, for example, T. H. James, The Theory of the Photographic Process, 4th edition, pages 335 to 362, 1977, published by MacMillan Publishing Co., Ltd.)

By color development, areas contacted with the fogging agent give blackening by silver and coloring by a coloring material. Hence, in color development, a higher optical density than blackening by silver alone is obtained. With developed areas obtained by color development, the light absorption due to dye formation can be measured by light of the light absorption wavelength(s) of the dyes.

Development may also be performed in the presence of a known accelerator for accelerating formation of nucei, as disclosed in Unexamined Japanese Patent Publication No. 226652/1988.

After development, a stopping solution may be used in this invention and, as the stopping solution, an aqueous solution containing a compound capable of stopping development such as a pH reducing agent (e.g. a mineral acid, an organic acid, etc.) or a mercapto compound can be used. Also, when the fixing solution used is an acid fixing solution, i.e. having a sufficiently low pH for a stopping the development, the stopping solution may be omitted.

As fixing solutions, those having compositions conventionally used in photographic processing can be employed, e.g. as fixing agents, organic sulfur compounds such as thiosulfates, thiocyanates and other organic sulfur compounds that are known as having a fixing effect can be employed. The fixing solution can also contain water soluble aluminum salts as a hardening agent.

In this invention, measurement of the photographic density or color density after development can be sufficiently performed by means of an optical densitometer as is used for measuring the density of conventional photographic images and hence measurement can be performed simply at a low cost. In the case of measuring optical density, the photographic density or color density can be measured by inserting a proper color filter in an optical path. Usually the photographic density or color density of a light sensitive element which has been finished via conventional photographic processing and dried is measured; however, the photographic density or color density of the light sensitive element immersed in a processing solution may be measured at the end of development, at the end of stopping, or at the end of fixing.

EXAMPLES

The present invention will be described more specifically with reference to an example thereof.

(1) Synthesis of Synthetic Substrate for Measuring Amylase (Biotin-G$_7$PAP-Nucleating Agent)

A synthetic substrate, Compound (I), for use in the measurement of amylase was synthesized through the

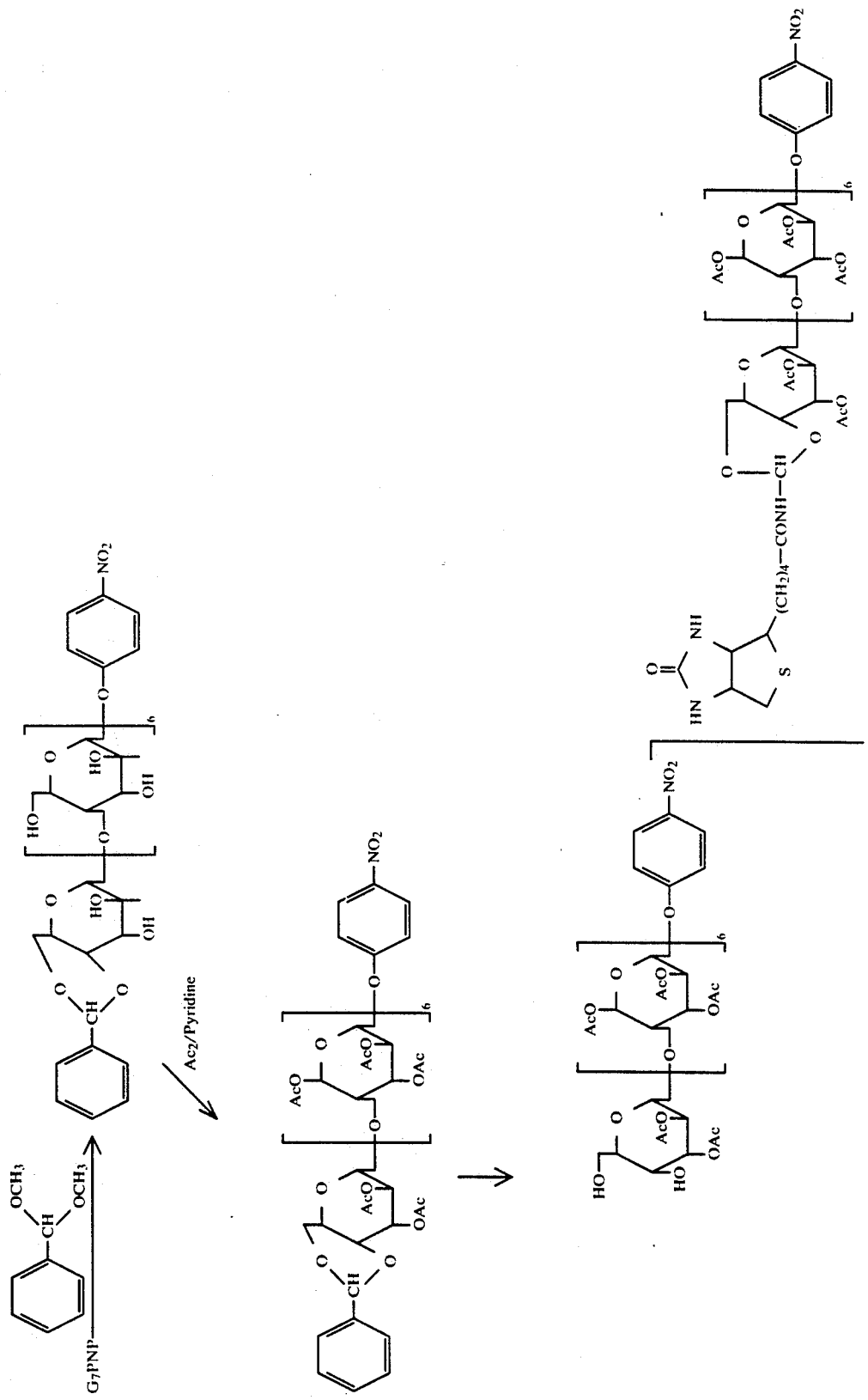

-continued
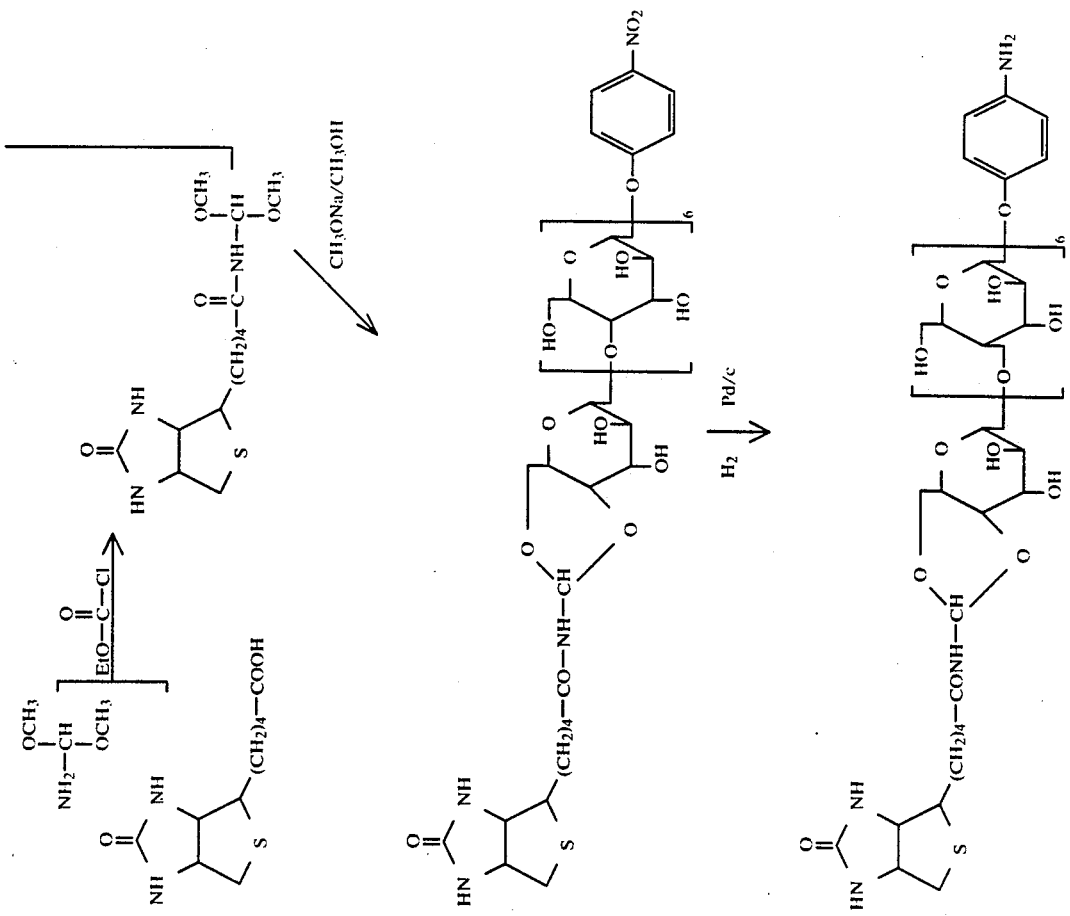

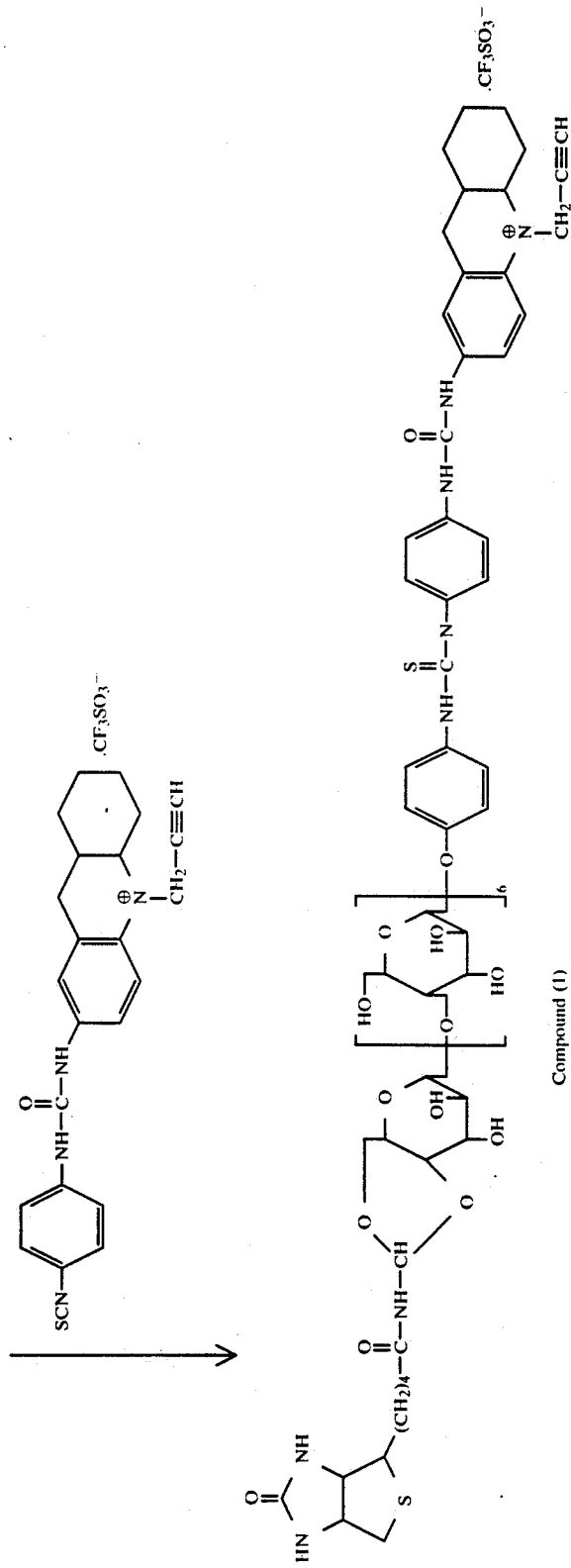

(2) Enzyme Reaction

One mg of α-amylase (produced by Belinger Manheim Yamanouchi Co., Ltd.) extracted from the porcine pancrease was dissolved in 10 ml of a 0.05 M phosphate buffer having a pH value of 6.0. The solution was diluted to obtain diluted solutions respectively having the concentration of 10 pg/ml, 100 pg/ml, 1 ng/ml, 10 ng/ml, 100 ng/ml and 1000 ng/ml (corresponding respectively to $1.9 \times 10^{-13}$ mole/l to $1.9 \times 10^{-8}$ mole/l). 100 μl for each of these diluted solutions was mixed with 900 μl of a $10^{-4}$ mole/l solution of the Compound (I) in a phosphate buffer and the mixture was incubated in a constant temperature bath (37° C.) for reaction. As a blank or control, 100/μl of the phosphate buffer solution was mixed with 900 μl of the $10^{-4}$ mole/l solution of the Compound (I) and processed similarly as the sample solutions.

(3) Separation of Unreacted substrate

Small columns (Volume of Gel: 200 μl, Viotin Binding Capacity: 1 μg) each containing avidin-agarose equilibrated by a 0.125 M pyridine acetate solution (pH: 6.0, containing 0.5M of NaCl) were prepared. Each of the sample solutions, after reacting for 20 minutes at the step (2), was charged in each small column. 100 μl of the pyridine acetate buffer was poured on the upper empty region of the small column to elute the solution by the atmospheric pressure, and then the eluate was transferred to a small test tube.

(4) 40 μl of the eluate obtained at the step (3) was spotted on a silver halide film having the construction as described hereinafter and allowed to stand for 5 minutes, and then the spot was developed at 25° C. for 2 minutes using Hilendol (produced by Fuji Photo Film co., Ltd.) added with a 4M aqueous solution of sodium hydroxide to adjust the pH value to pH 13. The blackened density of the developed silver was measured. The result are shown in the following Table.

| concentration of Amylase in the Sample | Measured Optical Density |
|---|---|
| 0 | 0.32 |
| 10 pg/ml | 0.35 |
| 100 pg/ml | 0.43 |
| 1 ng/ml | 0.76 |
| 10 ng/ml | 1.12 |
| 100 ng/ml | 1.46 |
| 1 μg/ml | 1.56 |

Construction of Silver Halide Film

Silver Halide Grains: Flat plate shape grains having an average grain size of 2.2 μm φ×0.16 μm thick Composition of Silver Halide: AgBr Layer Construction:
  Protection Layer: Thickness: 1 μm, Binder: Gelatin
  Photographic Emulsion Layer:
  Thickness: 5 μm
  Binder: Gelatin (70%)-Polyacrylamide (30%)
Water Absorbing Layer:
  Thickness: 10 μm
  Binder: Gelatin (90%)-Vinylpyrrolidone (10)-Acrylic Acid(90)-Copolymer (10%)

It should be appreciated from the results set forth in the Table that trace amylase can be quantitatively determined by the use of the synthetic substrate and the method provided by this invention.

What is claimed is:

1. A substrate for use in a quantitative measurement of an enzyme, characterized in that said substrate has a molecular structure comprising:
    at least one structure (A) having a contact site and a recognition or binding site for reaction with the enzyme to be assayed;
    at least one labelling structure (B) capable of forming photographically developable nuclei upon contact with silver halide grains after contacting the substrate with the enzyme to be assayed; and
    at least one structure (C) cable of being specifically adsorbed by an absorbent.
    wherein said at least one labelling structure (B) is linked through said at least one structure (A) with at least one structure (C) in a manner that does not destroy the reactivity of the at least one structure (A) with the enzyme to be assayed, and wherein said at least one structure (C) is capable of being released from the substrate upon reaction of the substrate with the enzyme to be assayed.

2. The substrate of claim 1, wherein said substrate is a high molecular weight polymer including two or more of said structure (B) which are linked to each other and two or more of said structures (C) which are linked to each other, said linked two or more structure (B) and said linked two or more structures (C) being linked to each other through two or more of said structures (A).

3. The substrate of any of claims 1 or 2, wherein said at least one structure (A) is selected from the group consisting of glucosides, peptides, nucleic acids, and lipids.

4. The substrate of any of claim 1 or 2, wherein said at least one structure (C) is selected from the group consisting of antigens and haptens.

5. The substrate of any of claims 1 or 2, wherein said at least one structure (C) is biotin.

6. The substrate of claim 4, wherein said hapten is a dinitrophenyl group.

7. The substrate of claim 4, wherein said antigen is fluorescein.

8. The substrate 4, wherein said antigen is thyroxine.

9. A method for assaying a sample to determine quantitatively at least one of enzyme activity and quantity of an enzyme comprising the steps of:
    (a) providing a substrate having a molecular structure which comprises:
        at least one structure (A) having a contact site and a recognition or binding site for reaction with the enzyme to be assayed;
        at least one labelling structure (B) capable of forming photographically developable nuclei upon contact with silver halide grains after contacting the substrate with the enzyme to be assayed; and
        at least one structure (C) capable of being specifically adsorbed by an adsorbent;
        wherein said at least one labelling structure (B) is linked through said at least one structure (A) with said at least one structure (C) in a manner that does not destroy the reactivity of the at least one structure (A) with the enzyme to be assayed, and wherein said at least one structure (C) is capable of being released from the substrate upon reaction of the substrate with the enzyme to be assayed;
    (b) contacting a sample with said substrate under conditions for enzymatic reaction;
    (c) separating the reaction product containing said at least one labelling structure (B) from the excess unreacted substrate by contacting the reacted sample with the adsorbent;

(d) contacting either the reaction product separated at the step (c) or the excess unreacted substrate separated at the step (c) with silver halide;

(e) photographically developing either or both the reaction product and the excess unreacted substrate resulting from the step (d); and (f) measuring the optical density of a silver image resulting from the step (e) and/or a colored dye resulting from the step (e).

10. The method of claim 9, wherein said substrate ia high molecular weight polymer including two or more of said structures (B) which are linked to each other and two or more of said structures (C) which are linked to each other, said linked two or more structures (B) and said linked two or more structures (C) being linked to each other through two or more of said structures (A).

11. The method of any of claims 9 or 10, wherein said at least one structure (A) is selected from the group consisting of glucosides, peptides, nucleic acids, and lipids.

12. The method of any of claims 9 or 10, wherein said at least one structure (C) is selected from the group consisting of antigens and haptens.

13. The method of any of claim 9 or 10, wherein said at least one structure (C) is biotin.

14. The method of claim 12, wherein said hapten in a dinitrophenyl group.

15. The method of claim 12, wherein said antigen is fluorescein.

16. The method of claim 12, wherein said antigen is thyroxine.

17. The method of any of claims 9 or 10, wherein said enzyme to be assayed is an enzyme introduced as a label to an antigen, antibody or an $F_c$ receptor of bacterium.

18. The method of any of claims 9 or 10, wherein said enzyme to be assayed is an enzyme introduced as a label to a DNA probe.

19. The method of any of claims 9 or 10, wherein said at least one structure (A) is an oligosaccharide.

20. The method of claim 9, wherein said adsorbent is immobilized with a carrier.

21. The method of claim 9, wherein the separating of the step (c) comprises liquid chromatography.

* * * * *

UNITED STATES PATENT AND TRADEMARK OFFICE
CERTIFICATE OF CORRECTION

PATENT NO. : 5,300,421

DATED : April 5, 1994

INVENTOR(S) : Nobuhito Masuda et al

It is certified that error appears in the above-identified patent and that said Letters Patent is hereby corrected as shown below:

Col. 8, lines 33 and 34, delete "unsubstitutred", insert --unsubstituted--.

Col. 9, line 27, after "No." insert --17626--.

Col. 10, line 3, delete "froth", insert --f... 1--.

Col. 15, line 64, delete "N-III", insert --N-II--.

Col. 18, line 10, delete "IO".

Col. 25, line 45, after "No.", insert --821,251--.

UNITED STATES PATENT AND TRADEMARK OFFICE
CERTIFICATE OF CORRECTION

PATENT NO. : 5,300,421

DATED : April 5, 1994

INVENTOR(S) : Nobuhito Masuda et al

It is certified that error appears in the above-identified patent and that said Letters Patent is hereby corrected as shown below:

Col. 26, line 23, delete "adosrbent", insert --adsorbent--.

Col. 27, line 1, delete "charactristic", insert --characteristic--;

Col. 27, line 55, delete "which is the compound as", insert --as the compound which is--.

Col. 29, line 36, delete "ypical", insert --typical--.

Col. 30, line 47, delete "separtely", insert --separately--.

Col. 31, line 25, delete "pluraility", insert --plurality--;

UNITED STATES PATENT AND TRADEMARK OFFICE
CERTIFICATE OF CORRECTION

PATENT NO. : 5,300,421
DATED : April 5, 1994
INVENTOR(S) : Nobuhito Masuda et al It is certified that error appears in the above-identified patent and that said Letters Patent is hereby corrected as shown below:

Col. 31, line 30, delete "blacket", insert --blacken--.

Col. 32, line 30, delete "silve", insert --silver--.

Col. 34, line 53, delete "nucei", insert --nuclei--.

Col. 36, line 14, after "the" insert --synthesis process set forth below.--.

Col. 44, line 41, after "substrate" insert --of claim--.

Col. 45, line 12, delete "ia", insert --is--.

Signed and Sealed this

Eleventh Day of October, 1994

*Attest:*

BRUCE LEHMAN

*Attesting Officer*     Commissioner of Patents and Trademarks